(12) United States Patent
Crapo et al.

(10) Patent No.: US 8,765,729 B2
(45) Date of Patent: Jul. 1, 2014

(54) CANCER THERAPY

(75) Inventors: James D. Crapo, Englewood, CO (US); Brian J. Day, Englewood, CO (US); Ines Batinic-Haberle, Durham, NC (US); Richard Gammans, Research Triangle Park, NC (US); Zeljko Vusjaskovic, Durham, NC (US)

(73) Assignees: Aeolus Sciences, Inc., Laguna Niguel, CA (US); Duke University, Durham, NC (US); National Jewish Medical and Research Center, Denver, CO (US)

( * ) Notice: Subject to any disclaimer, the term of this patent is extended or adjusted under 35 U.S.C. 154(b) by 1448 days.

(21) Appl. No.: 11/558,408

(22) Filed: Nov. 9, 2006

(65) Prior Publication Data
US 2007/0149498 A1  Jun. 28, 2007

Related U.S. Application Data

(62) Division of application No. 10/051,367, filed on Jan. 22, 2002, now abandoned.

(60) Provisional application No. 60/262,390, filed on Jan. 19, 2001.

(51) Int. Cl.
*A61K 31/555* (2006.01)
*A61K 31/33* (2006.01)

(52) U.S. Cl.
USPC ............................ 514/185; 514/183; 514/184

(58) Field of Classification Search
USPC ......................................... 514/183, 184, 185
See application file for complete search history.

(56) References Cited

U.S. PATENT DOCUMENTS

| | | | |
|---|---|---|---|
| 4,376,174 A | * | 3/1983 | Itoh et al. ...................... 523/456 |
| 4,614,723 A | | 9/1986 | Schmidt |
| 4,657,902 A | | 4/1987 | Kappas et al. |
| 4,746,735 A | | 5/1988 | Kruper, Jr. et al. |
| 4,758,422 A | | 7/1988 | Quay |
| 4,829,984 A | | 5/1989 | Gordon |
| 4,837,221 A | | 6/1989 | Bonnett |
| 4,851,403 A | | 7/1989 | Picker et al. |
| 4,866,054 A | | 9/1989 | Dori et al. |

(Continued)

FOREIGN PATENT DOCUMENTS

| | | |
|---|---|---|
| CA | 2359116 | 7/2000 |
| EP | 0 127 797 | 12/1984 |

(Continued)

OTHER PUBLICATIONS

Rabbani, Zahid N. et al., *Low molecular weight catalytic metalloporphyrin antioxidant AEOL 10150 protects lungs from fractionated radiation*, Free Radical Research, Nov. 2007, 41(11):1273-82.

(Continued)

*Primary Examiner* — Shengjun Wang
(74) *Attorney, Agent, or Firm* — Kilpatrick Townsend & Stockton LLP

(57) ABSTRACT

The present invention relates, in general, to cancer therapy, and, in particular, to a method of preventing or treating cancer using low molecular weight antioxidants (e.g., mimetics of superoxide dismutase (SOD)) as the active agent or as a chemo- and/or radio-protectant. The invention also relates to compounds and compositions suitable for use in such a method.

4 Claims, 32 Drawing Sheets

B16 Melanoma tumor - SOD mimetic treatment

(56) References Cited

U.S. PATENT DOCUMENTS

| | | | |
|---|---|---|---|
| 4,885,114 A | 12/1989 | Gordon et al. | |
| 4,892,941 A | 1/1990 | Dolphin et al. | |
| 4,895,719 A | 1/1990 | Radhakrishnam | |
| 4,963,367 A | 10/1990 | Ecanow | |
| 5,010,073 A | 4/1991 | Kappas et al. | |
| 5,051,337 A | 9/1991 | Sakoda et al. | |
| 5,087,438 A | 2/1992 | Gordon | |
| 5,109,016 A | 4/1992 | Dixon et al. | |
| 5,130,245 A | 7/1992 | Marklund et al. | |
| 5,162,519 A | 11/1992 | Bonnett et al. | |
| 5,169,630 A | 12/1992 | Okaya et al. | |
| 5,171,680 A | 12/1992 | Mullenbach et al. | |
| 5,192,757 A | 3/1993 | Johnson et al. | |
| 5,192,788 A | 3/1993 | Dixon et al. | |
| 5,202,317 A | 4/1993 | Bruice | |
| 5,217,966 A | 6/1993 | Bruice | |
| 5,223,538 A | 6/1993 | Fridovich et al. | |
| 5,227,405 A | 7/1993 | Fridovich | |
| 5,236,914 A | 8/1993 | Meunier | |
| 5,236,915 A | 8/1993 | Fiel | |
| 5,248,603 A | 9/1993 | Marklund et al. | |
| 5,262,532 A | 11/1993 | Tweedle et al. | |
| 5,277,908 A | 1/1994 | Beckman et al. | |
| 5,281,616 A | 1/1994 | Dixon et al. | |
| 5,284,647 A | 2/1994 | Niedballa | |
| 5,366,729 A | 11/1994 | Marklund et al. | |
| 5,403,834 A | 4/1995 | Malfroy-Camine et al. | |
| 5,405,369 A | 4/1995 | Selman et al. | |
| 5,472,691 A | 12/1995 | Marklund et al. | |
| 5,493,017 A | 2/1996 | Thieren et al. | |
| 5,563,132 A | 10/1996 | Bodaness | |
| 5,599,924 A | 2/1997 | Thieren et al. | |
| 5,604,199 A | 2/1997 | Funanage | |
| 5,610,293 A | 3/1997 | Riley et al. | |
| 5,637,578 A | 6/1997 | Riley et al. | |
| 5,674,467 A | 10/1997 | Maier et al. | |
| 5,747,026 A | 5/1998 | Crapo | |
| 5,767,272 A | 6/1998 | Wijesekera et al. | |
| 5,824,781 A * | 10/1998 | Hsia | 530/385 |
| 5,834,509 A | 11/1998 | Malfroy-Camine et al. | |
| 5,874,421 A | 2/1999 | Riley et al. | |
| 5,948,771 A | 9/1999 | Danziger | |
| 5,976,498 A | 11/1999 | Neumann et al. | |
| 5,976,551 A | 11/1999 | Mottez et al. | |
| 5,994,339 A | 11/1999 | Crapo et al. | |
| 5,994,410 A | 11/1999 | Chiang et al. | |
| 6,013,241 A | 1/2000 | Marchal et al. | |
| 6,046,188 A | 4/2000 | Malfroy-Camine et al. | |
| 6,060,467 A | 5/2000 | Buelow et al. | |
| 6,084,093 A | 7/2000 | Riley et al. | |
| 6,087,493 A | 7/2000 | Wheelhouse et al. | |
| 6,103,714 A | 8/2000 | Fridovich et al. | |
| 6,127,356 A | 10/2000 | Crapo et al. | |
| 6,180,620 B1 | 1/2001 | Salvemini | |
| 6,204,259 B1 | 3/2001 | Riley et al. | |
| 6,214,817 B1 | 4/2001 | Riley et al. | |
| 6,245,758 B1 | 6/2001 | Stern et al. | |
| 6,372,727 B1 | 4/2002 | Crow et al. | |
| 6,395,725 B1 | 5/2002 | Salvemini | |
| 6,403,788 B1 | 6/2002 | Meunier et al. | |
| 6,417,182 B1 | 7/2002 | Abrams et al. | |
| 6,544,975 B1 | 4/2003 | Crapo et al. | |
| 6,548,045 B2 | 4/2003 | Sakata et al. | |
| 6,566,517 B2 | 5/2003 | Miura et al. | |
| 6,602,998 B2 | 8/2003 | Kobuke et al. | |
| 6,624,187 B1 | 9/2003 | Pandey et al. | |
| 2,951,799 A1 | 11/2007 | Sharp | |
| 2002/0058643 A1 | 5/2002 | Cherian et al. | |

FOREIGN PATENT DOCUMENTS

| | | | |
|---|---|---|---|
| EP | 0 186 962 | | 7/1986 |
| EP | 0 289 667 | * | 4/1987 |
| EP | 0 282 899 | | 9/1988 |
| EP | 0 284 645 | | 10/1988 |
| EP | 0 336 879 | | 10/1989 |
| EP | 0 337 601 | | 10/1989 |
| EP | 0 345 171 | | 12/1989 |
| EP | 0 414 915 | | 3/1991 |
| EP | 0 462 836 | | 12/1991 |
| EP | 0 524 161 | | 1/1993 |
| EP | 0 532 327 | | 3/1993 |
| FR | 2 676 738 | | 11/1992 |
| JP | 63250392 | | 10/1988 |
| JP | 02289844 | | 11/1990 |
| JP | 03273082 | | 12/1991 |
| JP | 6-501694 | | 2/1994 |
| JP | 07238023 | A | 9/1995 |
| JP | 09176187 | A | 7/1997 |
| JP | 2000-169499 | | 6/2000 |
| WO | 90/10694 | | 9/1990 |
| WO | 91/04315 | | 4/1991 |
| WO | 91/19977 | | 12/1991 |
| WO | 92/05178 | | 4/1992 |
| WO | WO9205178 | | 4/1992 |
| WO | 92/07935 | | 5/1992 |
| WO | 92/08482 | | 5/1992 |
| WO | 92/15099 | | 9/1992 |
| WO | 93/02090 | | 2/1993 |
| WO | 94/04614 | | 3/1994 |
| WO | 94/05285 | | 3/1994 |
| WO | 95/10185 | | 4/1995 |
| WO | 95/31197 | | 11/1995 |
| WO | 96/09038 | | 3/1996 |
| WO | 96/09053 | | 3/1996 |
| WO | 96/40148 | | 12/1996 |
| WO | 96/40223 | | 12/1996 |
| WO | 97/06824 | | 2/1997 |
| WO | 97/06830 | | 2/1997 |
| WO | 97/06831 | | 2/1997 |
| WO | 97/33588 | | 9/1997 |
| WO | 97/33877 | | 9/1997 |
| WO | 98/33503 | | 8/1998 |
| WO | 98/58636 | | 12/1998 |
| WO | 99/23097 | | 5/1999 |
| WO | WO99/23097 A1 | | 5/1999 |
| WO | WO 99/55388 | | 11/1999 |
| WO | 00/04868 | | 2/2000 |
| WO | 00/19993 | | 4/2000 |
| WO | 00/23568 | | 4/2000 |
| WO | 00/43395 | | 7/2000 |
| WO | WO00/43395 A1 | | 7/2000 |
| WO | 00/72893 | | 12/2000 |
| WO | 00/75144 | | 12/2000 |
| WO | 01/26655 | | 4/2001 |
| WO | 01/96345 | | 12/2001 |
| WO | 02/060383 | | 8/2002 |
| WO | 02/098431 | | 12/2002 |
| WO | 03/103680 | | 12/2003 |

OTHER PUBLICATIONS

Rabbani, Zahid N. et al., *Long-term administration of a small molecular weight catalytic metalloporphyrin antioxidant, AEOL 10150, protects lungs from radiation-induced injury*, Int. J. Radiation Oncology Biol. Phys., 2007, 67(2):573-80.

Longo et al., "The Synthesis and Some Physical Properties of ms-Tetra(pentafluorophenyl)-porphin and msTetraphenylporphines (1)", Notes 6:927-931 (1969).

Lord, "Redox characteristics of nickel and palladium complexes of the open-chain tetrapyrrole octaethylbilindione: a bliverdin model", Inorg. Chem. 39(6):1128-1134 (2000).

Louati et al., "Homophophyrines: Effets D'Une Coupure De Conjugaison Cyclique Sur La Reactivite Redox Des Porphyrines", Nouv. J. Chim. 2:163-168 (1978).

Lowe et al., "Comparison of the cardiovascular effects of two novel superoxide dismutase mimetics, SC-55858 and SC-54417, in conscious dogs", European Journal of Pharmacoloty 304:81-86 (1996).

Mabley et al., "Part II: Beneficial Effects of the Peroxynitrite Decomposition Catalyst FP15 in Murine Models of Arthritis and Colitis", Molecular Medicine 8(10):581-590 (2002).

(56) References Cited

OTHER PUBLICATIONS

Mackensen et al., "Neuroprotection from Delayed Postischemic Administration of a Metalloporphyrin Catalytic Antioxidant", The Journal of Neuroscience 21(13):4582-4592 (2001).

Madakyan et al., "New watersoluble metal complexes of meso-tetrakis[3-N-(2'-hydroxy ethyl)pyridyl]porphyrins and their pharmacological activity", Arm. Khim. Zh. 42(11):724-728—Chemical Abstracts 113:653—Abstract No. 114907h, 1990.

Madakyan et al., "Some metal complexes of meso-tetrakis (3-N-substituted pyridyl) porphyrins and their bioactivity", Arm. Khim. Zh. 42(10):642-646 (1989).

Malinski et al., "Characterization of Conductive Polymeric Nickel(II) Tetrakis(3-methoxy-4-hydroxyphenyl)Porphyrin as an Anodic Material for Electrocatalysis", J. Electrochem. Soc. 138(7):2008-2015 (1991).

Marx, "Role of Gene Defect in Heredity ALS Clarified", Science 261:986 (1993).

McClune et al., "Catalysis of Superoxide Dismutation by Iron-Ethylenediaminetetraacetic Acid Complexes. Mechanism of the Reaction and Evidence for the Direct Formation of an Iron(III)-Ethylenediaminetetraacetic Acid Peroxo Complex from the Reaction of Superoxide with Iron(II)-Ethylenediaminetetraacetic Acid", Communications to the Editor, p. 5220-5222 (1977).

McCord et al., "Superoxide Dismutase-An Enzymic Function for Erythrocuprein", Biochemistry 492, p. 346, 1960.

McCord et al., Superoxide Dismutase an Enzymic Function for Erythrocuprein (Hemocuprein), The Journal of Biological Chemistry 244(22):6049-6055 (1969).

Milgrom et al., "Redox Behaviour of Phenolic Porphyrins in Basic Solutions: A Reappraisal", Free Rad. Res. 24 (1):19-29 (1996).

Milgrom, Facile Aerial Oxidation of a Porphyrin. Part 3. "Some Metal Complexes of meso-Tetrakis-(3,5-di-tbutyl-4-hydroxyphenyl)porphyrin", J. Chem. Soc. Perkin Trans. 11:71-79 (1988).

Miller, et al., "Langmuir-Blodgett Films Containing Porphyrins in a Well-Defined Environment.", Elsevier Sequoia/Printed in the Netherlands, XP-002390132, pp. 83-91 (1985).

Moisy et al., "Catalytic Oxidation of 2,6-Di-Terbutylphenol by Molecular Oxygen Electroassisted by Poly(Pyrrole Manganese-Porphyrin)", New J. Chem. 13:511-514 (1989).

Naruta et al., "High Oxygen-Evolving Activity of Rigidly Linked Manganese (III) Porphyrin Dimers. A Functional Model of Manganese Catalase", J. Am. Chem. Soc. 113:3595-3596 (1991).

Oberley et al., "Anticancer activity of metal compounds with superoxide dismutase activity", Agents and Actions 15 (5/6):535-538 (1984).

Obst et al., "Helicobacter pylori causes DNA damage in gastric epithelial cells", Carcinogenesis 21(6):1111-1115 (2000).

O'Hara et al., "Potentiation of radiation-induced cell kill by synthetic metalloporphyrins", Int. J. Radiat. Oncol. Biol. Phys. 16(4):1049-1052 (1989).

Ohkawa et al., "Assay for Lipid Peroxides in Animal Tissues by Thiobarbituric Acid Reaction", Analytical Biochemistry 95:351 (1979).

Oury et al., "Cold-induced Brain Edema in Mice", The Journal of Biological Chemistry 268(21):15394-15398 (1993).

Oury et al., "Establishment of Transgenic Mice Expressing Human Extracellular Superoxide Dismutase", American Review of Respiratory Disease 143(4):A515 (1991), International Conference Supplement Abstracts—No. 236.

Oury et al., "Extracellular superoxide dismutase, nitric oxide, and central nervous system 02 toxicity", Proc. Natl. Acad. Sci. USA 89:9715-9719 (1992).

Oury et al., "Immunocytochemical Localization of Extracellular Superoxide Dismutase in Human Lung", American Revew of Respiratory Disease 147(4):A713 (1993), International Conference Supplement Abstracts—No. 246.

Oury et al., "Transgenic Mice Superexpressing Human Extracellular Superoxide Dismutase Show Increased Resistance to Cold-induced Brain Edema, But are More Susceptible to Hyperbaric Oxygen", American Review of Respiratory Disease 145(4):A713 (1992), International Conference Supplement Abstracts—No. 211.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Parge et al., "Atomic structures of wild-type and thermostable mutant recombinant human Cu,Zn superoxide dismutase", Proc. Natl. Acad. Sci. USA 89:6109-6113 (1992).

Pasternack et al., "Aggregation of Nickel(II), Coppwer (II), and Zinc(II) Derivatives of Water-Soluble Porphyrins", Inorganic Chemistry 12(11):2606-2610 (1973).

Pasternack et al., "Catalyst of the Disproportionation of Superoxide by Metalloporphyrins III", Journal of Inorganic Biochemistry 15:261-267 (1981).

Pasternack et al., "On the Aggregation of Meso-Substituted Water-Soluble Porphyrins", Journal of American Chemical Society 94(13):4511-4517 (1972).

Pasternack et al., "Superoxide Dismutase Activities of an Iron Porphyrin and Other Iron Complexes", Journal of the American Chemical Society 101(4):1026-1031 (1979).

Patel et al., "Requirement for Superoxide in Excitotoxic Cell Death", Neuron 16:345-355 (1996).

Patel et al.., "Metalloporphyrin class of therapeutic catalytic antioxidants", TIPS Elsevier Trends Journal 20 (9):359-364(1999).

Peretz et al., "Chemical properties of water-soluble porphyrins 3. The reaction of superoxide radicals with some metalloporphyrins", Int. J. Radiat. Biol. 42(4):449-456 (1982).

Perez et al., "Spontaneous reduction of octadecyltetracyanoquinodimethane at the air-water interface in the presence of amphiphilic cations.", Elsevier Sequoia, 244:1043-1049 (1994) XP008066628.

Picker et al., "Cobalt(III) complexes of water soluble synthetic meso-substituted porphyrins as radiation sensitizers for oxic and hypoxic tumor cells", 8-Radiation 112:405 (1990) Abstract No. 112:73026d.

Pitie et al., "Oxidation at Carbon-1' of DNA Deoxyriboses by the Mn-TMPyP/KHSO5 System Results from a Cytochrome P-450-Type Hydroxylation Reaction", J. Am. Chem. Soc. 117:2935-2936 (1995).

Polson et al., "The Effect of Liver Transplantation in a 13-Year-Old Boy with Erythropoietic Protoporphyria", Transplantation 46(3):386-389 (1988).

Porteu et al., "Molecular engineering at the air-water interface: building up designed supermolecular assemblies with amphiphilic porphyrins", CAPLUS, Chemical Abstracts Service, XP-002390145, AN 1992:519030, 1992.

Porteu et al., "Supermolecular Engineering at the Air-Water Interface: Spatially Controlled Formation of Heterodimers from Amphiphillc Porphyrins and Porphyrazines through Specific Molecular Recognition.", J. Phys. Chem. 95:7438-7447 (1991) XP-002390131.

Registry Copyright 2004 ACS on STN, Registry No. 138025-71-5, Entered STN: Dec. 21, 1991.

Richards et al., "Observation of a Stable Water-Soluble Lithium Porphyrin", Inorg. Chem. 35:1940-1944 (1996).

Robertson, Jr. et al, "Does Copper-D-Penicillamine Catalyze the Disutatio of O2-?", Archives of Biochemistry and Biophysics 203(2) 830-831 (1980).

Rosenfeld et al., "Safety and pharmacokinetics of recombinant human superoxide dismutase administered intratracheally to premature neonates with respiratory distress syndrome", Pediatrics 97(Pt 1):811-817 (1996).

Ruaudel-Teixier et al., "Langmuir-Blodgett Films of Pure Porphyrins.", Elsevier Sequoia/Printed in the Netherlands, pp. 33-40, XP000986319 (1983).

Ruoslahti et al., "Arg—Gly—Asp: A Versatile Cell Recognition Signal", Cell 44:517-518 (1986).

Sari et al., "Interaction of Cationic Porphyrins with DNA: Importance of the Number and Position of the Charges and Minimum Structural Requirements for Intercalation", Biochemistry 29:4205-4215 (1990).

(56) References Cited

OTHER PUBLICATIONS

Schlozer et al., "Reactivity of Unsubstituted Porphin", German version: Angew. Chem. 87:388 (1975).
Dwyer et al., "Protective Properties of Tin- and Manganese-Centered Porphyrins Against Hydrogen PeroxideMediated Injury in Rat Astroglial Cells", J. Neurochem 71:2497 (1998).
Elangovan and Krishnan, "Photophysical properties of porphyrin amphiphiles bearing pyridinium alkyl groups", Chemical Physics Letters 194(1,2):139-146 (1992), XP000986304.
El-Far and Pimstone, "Selective in Vivo Tumor Localization of Uroporphyrin Isomer I in Mouse Mammary Carcinoma: Superiority over Other Porphyrins in a Comparative Study", Cancer Research 46:34390-4394 (1986).
Epp et al., "Superoxide Dismutase Activity of Manganese Chelates", 76-78 (1986).
Ex parte Giorgio Winters, Appeal No. 88-1423, Board of Appeals and Interferences, 1998 Pat. App. LEXIS 39; 11 U.S. P.Q.2D (BNA) 1387.
Ex parte William C. Levengood, Appeal No. 92/3654, Board of Appeals and Interferences, 1993 Pat. App. LEXIS 10; 28 U.S.P.Q.2D (BNA) 1300.
Fajer et al., "Tr-Cation Radicals and Dications of Metalloporphyrins", Journal of the American Chemical Society 92(11):3451-3459 (1970).
Falk, "Contributions to the chemistry of pyrrolic pigments", Tetrahedron 37(4):761-767 (1981).
Faulkner et al., "Characterization of Mn(III) Complexes of Linear and Cyclic Desferrioxamines as Mimics of Superoxide Dismutase Activity", Archives of Biochemistry and Biophysics 310(2):341-346 (1994).
Faulkner et al., Stable Mn(III) Porphyrins Mimic Superoxide Dismutase in Vitro and Substitute for It in Vivo, The Journal of Biological Chemistry 269(38):23471-23476 (1994).
Folz et al., "Extracellular Superoxide Dismutase (SODS): Tissue-Specific Expression, Genomic Characterization, and Computer-Assisted Sequence Analysis of the Human EC SOD Gene", Genomics 22:162-171 (1994).
Foran et al., "Effect of Electrolyte Concentration on Axial Anion Ligation in Manganese(III) mesa Tetraphenylporphyrin Chlorides", Inorg. Chem. 31:1463-1470 (1992).
Gassman et al., "Electronic Effects of Peripheral Substituents in Porphyrins: X-ray Photoelectron Spectroscopy and ab Initio Self-Consistent Field Calculations", J. Am. Chem. Soc. 114:9990-10000 (1992).
Gauuan et al., "Superoxide dismutase mimetics: synthesis and structure-activity relationship study of MnTBAP analogues", Bioorganic & Medicinal Chemistry 10(9):3013-3021 (2002).
Giraudeau et al., "Substiuent Effects in the Electroreduction of Porphyrins and Metalloporphyrins", Journal of the American Chemical Society 101(14):3857-3862 (1979).
Gonzalez et al., "EUK-8, a Synthetic Superoxide Dismutase and Catalase Mimetic, Ameliorates Acute Lung Injury in Endotexemic Swine", The Journal of Pharmacology and Experimental Therapeutics 275(2):798-806 (1995).
Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691-4699 (1995).
Groves and Marla, "Peroxynitrite-Induced DNA Strand Scission Mediated by a Manganese Porphyrin", J. Am. Chem. Soc. 117(37):9578-9579 (1995).
Halliwell, Barry, "The Superoxide Dismutase Activity of Iron Complexes", FEBS Letters 56(1):34-38 (1975).
Hambright et al., "An acid solvolysis kinetic study of manganese(II)-tetra(2-N-methylpyridyl)porphine", J. Inorg. Chem. 39:1102-1103 (1977).
Hambright et al., "Manganese(III) porphyrin isomers: polarography and stannous ion reduction kinetics", Porphyrin Chem. Adv., editor: Longo, [Pap. Porphyrin Symp.], pp. 284-292, Meeting Date 1977.
Hambright et al., "Synthesis and Characterization of New Isomeric Water-Soluble Porphyrins Tetra(2-Nmethylpyridyl)porphine and Tetra(3-N-methylpyridyl)porphine", Inorganic Chemistry 15(9):2314-2315 (1976).
Harriman et al., "Photochemistry of Manganese Porphyrins Part 2.—Photoreduction", pp. 1543-1552, 1979.
Harriman et al., "Photochemistry of Manganese Porphyrins", J. Chem. Soc. 275:1532-1542 (1979)_.
Hunt et al., "Amphiphilic peroxynitrite decomposition catalysts in liposomal assemblies", Chemistry & Biology 4(11):845-858 (1997).
Iamamoto et al., "Cationic ironporphyrins as catalyst in comparative oxidation of hydrocarbons: homogeneous and supported on inorganic matrices systems.", Journal of Molecular Catalysis, XP-002390128-XP-002390129, pp. 187-193 (1995).
Iamamoto et al., "Iron(III) Porphyrins Atropisomers as Catalysts for Cyclohexane Hydroxylations. A Biomimetical System.", Journal of Inorganic Biochemistry, XP-002390130, pp. 54, 55-66 (1994).
Iian et al., "Superoxide Dismuting Activity of an Iron Porphyrin", Inorg. Nucl. Chem. Letters 17(3/4):93-96 (1981) Couple, J. Phys. Chem. 86:1842-1849 (1982).
In Re Gerald McLaughlin, LEXSEE 443 F.2D 1392, No. 8474, United States Court of Customs and Patent Appeals, 58 C.C.P.A. 1310; 1971 CCPA Lexis 299; 170 U.S.P.Q. (BNA) 209.
Inoue et al., "Expression of a Hybrid Cu/Zn-type Superoxide . . . ," J. Bio. Chem., vol. 266, No. 25, pp. 16409-16414 (1991).
J Masatada et al., "Peroxide Decomposer", Patent Abstracts of Japan (1991)—Abstract.
Jin et al., "A new route to water soluble porphyrins: phosphonium and ammonium type cationic porphyrins and self-assembly", Chem. Commun., pp. 1939-1940 (1996).
Joester et al., "Superoxide Dismutase Activity of Cu2+-Amino Acid Chelates", FEBS Letters 25(1):25-28 (1972).
Kariya et al., "Superoxide Dismutase (SOD) Activity with Fe-chlorin e6-Na and Suppression of Malignant Tumor Growth in Rats", Cancer Biotheraphy 10(2):139-145 (1995).
Kaufmann et al., "Separation of the Rotational Isomers of Tetrakis(N-methyl-2-pyridiniumyl)porphyrin and Crystal Sturcture of a,a,a,R-(Tetrakis(N-methyl-2-pyridiniumyl)porphyrin)copper Hexacyanoferrate", Inorg. Chem. 34:5073-5079 (1995).
Keinan et al., "Catalytic Antibodies. Circular Dichroism and UV-Vis Studies of Antibody-Metalloporphyrin Interactions", Inorg. Chem. 31:5433-5438 (1992).
Kobayashi et al., "Oxidative Stress Relief for Cancer-Bearing Hosts by the Protein-Bound Polysaccharide of Coriolus versicolor QUEL with SOD Mimicking Activity", Cancer Biotherapy 9(1):55-62 (1994).
Koerner "Carbon monoxide production during the oxygenation of cobalt complexes of linear etrapyrroles", Inorg. Chem. 37(5):982-988 (1998).
Konorev et al., "Cell-Permeable Superoxide Dismutase and Glutathione Peroxidase Mimetics Afford Superior Protection against Doxorubicin-Induced Cardiotoxicity: The Role of Reactive Oxygen and Nitrogen Intermediates", Archives of Biochemistry and Biophysics 368(2):421-428 (1999).
Kumar et al., "Radioprotection by Antioxidant Enzymes and Enzyme Mimetics", Pharmac. Ther. 39:301-309 (1988).
Laehdesmaeki et al., "Detection of Oxygen Consumption of Cultured Adherent Cells by Bead Injection Spectroscopy", Analytical Chemistry 71(22):5248-5252 (1999).
Lappin, "Part III Bioinorganic Studies", Inorganic Reaction Mechanisms 7:334-343 (1981).
Lee and Smith, "Syntheses of symmetrically substituted 5-alkyl- and 5-aryl-dihydrodipyrrins and of porphyrins and bisporphyrins therefrom", J. Chem. Soc. Perkin Trans 1:1215-1227 (1997).
Lee et al., "Rapid decomposition of peroxynitrite by manganese porphyrin-antioxidant redox couples", Bioorganic & Medical Chemistry Letters 7(22):2913-2918 (1997).
Leonidas et al., "5,10,15,20-Tetrakis(α,α,α,α-o-(N-tert-butyl-carbamoyl)phenyl)porphyrin: Syntheses and Redox Properties of Zinc(II) and Copper(II) Complexes", J. Org. Chem. 54:6135-6138 (1989).

(56) References Cited

OTHER PUBLICATIONS

Libby et al., "Cationic Porphyrin Derivatives As Inhibitors of Polyamine Catabolism", Biochemical Pharmacology 50 (9):1527-1530 (1995).
Lindsey et al., "Rothemund and Adler-Longo Reactions Revisited: Synthesis of Tetraphenylphorins under Equilibrium Conditions", J. Org. Chem. 52:827-836 (1987).
Lindsey et al., "Synthesis of tetraphenylporphyrins under very mild conditions", Tetrahedron Letters 27 (41):4969-4970 (1986).
Lindsey et al., i252Cf Plasma Desorption Mass Spectrometry in the Synthesis of Porphyrin Model Systems, Anal. Chem. 64(22):2804-2814 (1992).
Liochev et al., A Cationic Manganic Porphyrin Inhibits Uptake of Paraquat by *Escherichia coil*, Archives of Biochemistry and Biophysics 321(1):271-275 (1995).
Schneider et al., "Ligand-Porphyrin Complexes: Quantitative Evaluation of Stacking and Ionic Contributions", J. Org. Chem. 59:7464-7472 (1994).
Sharma et al., "Synthesis of amphiphilic 5-(4-N-alkylpyridiniumyl)-10,15,20-triphenylporphyrins and their aggregational properties in different solvent systems", Chemical Abstracts vol. 123, No. 1 (1995)—Abstract No. 9222q.
Sheldon, Chapter 1 in Metalloporphyrins in Catalytic Oxidations, Marcel Dekker, Inc. (1994).
Shimanovich et al., "Mn(II)-Texaphyrin as a Catalyst for the Decomposition of Peroxynitrite", J. Am. Chem. Soc. 123:3613-3614 (2001).
Simone, "Cecil Textbook of Medicine" 21st Edition, 2000, pp. 1029-1081.
Solomon et al., "Chemical properties of Water-Soluble Porphyrins. 2. The Reaction of Iron(III) Tetrakis(4-Nmethylpyridyl)porphyrin with the Superoxide Radical Dioxygen Couple", J. Phys. Chem. 86:1842-1849 (1982).
Song et al., "Anti-HIV activities of anionic metalloporphyrins and related compounds", Antiviral Chemistry and Chemotherapy 8(2):85 (1997).
Sonis et al., "AEOL 10150, a catalytic antioxidant, reduces the incidence and duration of radiation-induced oral mucositis in a hamster", European Journal of Cancer, Pergamon Press, Oxford GB, vol. 37, S361 (2001)—Abstract.
Sorenson, John R.J., "Copper Chelates as Possible Active Forms of the Antiarthritic Agents", Journal of Medicinal Chemistry 19(1):135-148 (1976).
Spasojevic et al., "Manganese(III) complexes with porphyrins and related compounds as catalytic scavengers of superoxide", Inorganica Chimica Acta 317:230-242 (2001).
Stralin et al., "Effects of Oxidative Stress on Expression of Extracellular Superoxide Dismutase, CuZnSuperoxide Fibroblast", Biochem. J. 298:347-352 (1994).
Szabo et al., "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82-86 (1996).
Szabo et al., "Part I: Pathogenetic Role of Peroxynitrite in the Development of Diabetes and Diabetic Vascular Complications: Studies With FP15, A Novel Potent Peroxynitrite Decomposition Catalyst", Molecular Medicine 8 (10):571-580 (2002).
Szabo et al., "Peroxynitrite Is Involved in the Pathogenesis of the Vascular Contractile and Energetic Failure in Endotoxic Shock", Shock Society Meeting (1996).
Tjahjono et al., "Cationic porphyrins bearing diazolium rings: synthesis and their interaction with calf thymus DNA", Biochemica et Biophisica Acta 1472:333-343 (1999).
Tsan, M-F., "Superoxide Dismutase and Pulmonary Oxygen Toxicity," XP-002074505, pp. 286-290, PSEBM 1993.
Tsvetkov et al., "Infrared spectra of copper complexes of tetraphenylporphyrin", Izvestiya Vysshikh Uchebnykh Zavedenij, Khimiya I Khimicheskaya Tekhnologiya 27(7)):782-785 (1984)—English Abstract.

Vergeldt et al., "Intramolecular Interactions in the Ground and Excited State of Tetrakis(N-methylpyridyi) porphyrins", J. Phys. Chem. 99:4397-4405 (1995).
Vinogradov et al., "Palladium catalyzed carbonylation of Br-substituted porphyrins", Tetrahedron Letters 39 (49):8935-8938 (1998).
Vodzinskii et al., "Porphyrines and Their Derivatives. XX. Synthesis and Properties of 2-Nitro-5,10,15,20 tetraherylporphyrins", Russian Journal of Organic Chemistry 34(6):882-885 (1998).
Walker et al., "Models of the cytochromes b. 5. EPR Studies of low-spin iron(III) tetraphenylporphyrins", Journal of the American Chemical Society 106(23):6888-6898 (Feb. 13, 1984).
Wang et al., Structure of LB film of 5,10,15,20-tetra(p-ethoyycarbonphenyl)porphyrin, Yingyong Huaxue 10(2):87-88 (1993)—Engish Abstract.
Weinraub et al., "Chemical Properties of Water-Soluble Porphyrins. 1. Equilibria between Some Ligands and Iron (III) Tetrakis (4-N-methylpyridyl)porphyrin", J. Phys. Chem. 86:1839-1842 (1982).
Weinraub et al., "Chemical properties of water-soluble porphyrins. 5. Reactions of some manganese (III) porphyrins with the superoxide and other reducing radicals", Int. J. Radiat. Biol. 50(4):649-658 (1986) (Abs).
Weiss et al., "Evaluation of Activity of Putative Superoxide Dismutase Mimics", The Journal of Biological Chemistry 268(31):23049-23054 (1993).
Weiss et al., "Manganese-based Superoxide Dismutase Mimetics Inhibit Neutral Infiltration in Vivo", The Journal of Biological Chemistry 271(42):26149-26156 (1996).
Werringloer et al., "The Integration of Divalent Copper and the Microsomal Electron Transport System", The Journal of Biological Chemistry, 254(23):11839-11846 (1979).
Wheelhouse et al., "Cationic Porphyrins as Telomerase Inhibitors; the Interaction of Tetra-(N-methyl-4pyridyl) porphine with Quadruplex DNA", J. Am. Chem. Soc. 120(13):3261-3262 (1998).
White et al., "A Highly Stereoselective Synthesis of Epothilone B", J. Org. Chem. 64:684-685 (1999).
Winkelman, James, "The Distribution of Tetraphenylporphinesulfonate in the Tumor-bearing Rat", Cancer Research 22:589-596 (1962).
Wolberg et al., Electrocical and Electron Paramagnetic Resonance Studies of Metalloporphyrins and Their Electrochemical Oxidation Products:, Journal of the American Chemical Society 92(10):2982-2990 (1970).
Yu et al., "Electrocatalytic reduction of nitric oxide by water-soluble manganese porphyrins", Journal of Electroanalytical Chemistry 368:323-327 (1994).
Yue et al., "Carvedilol, a New Vasodilator and Beta Adrenoceptor Antagonist, is an Antioxidant and Free Radical Scavenger", The Journal of Pharmacology and Experimental Therapeutics 263:(1992).
Zahedi, "Semiempirical molecular orbital calculations of biliverdin: study of dynamics and energetics of the self-association of a two-electron oxidation product", Theochem. 531:79-88 (2000).
Archibald et al., Investigations of the State of the Manganese in *Lactobacillus plantarum*, Archives of Biochemistry and Biophysics 215(2):589-596 (1982).
Archibald et al., Manganese and Defenses against Oxygen Toxicity in *Lactobacillus plantarum*, Journal of Bacteriology 145(1):442-451 (1981).
Archibald et al., Manganese, Superoxide Dismutase, Oxygen Tolerance in Some Lactic Acid Bacteria, Journal of Bacteriology 146(3):928-936 (1981).
Archibald et al., The Scavenging of Superoxide Radical by Manganous Complex: In Vitro, Archives of Biochemistry and Biophysics 214(2):452-463 (1982).
Balch, "Geometric and electronic structure and dioxygen sensitivity of the copper complex of octaethylbilindione, a biliverdin analog", J. Am. Chem. Soc. 115(25):12206-12207 (1993).
Balch, "Isolation and characterization of an iron biliverdin-type complex that is formed along with verdohemochrome during the coupled oxidation of iron (II) octaethylporphyrin", Am. Chem. Soc. 115(20):9056-9061 (1993).

(56) References Cited

OTHER PUBLICATIONS

Balch, "Solid-state self-association of the two-electron oxidation product of a biliverdin analogue", J. Chem. Soc. Chem. Commun. 6:643-644 (1995).
Bamford et al., "The Squalestatins: Synthesis and Biological Activity of Some C3-Modified Analogues; Replacement of a Carboxylic Acid or Methyl Ester with an Isoelectric Heterocyclic Functionality", J. Med. Chem. 38:3502-3513 (1995).
Barnitz-McLaughlin et al., "Reactions of Fe01(meso-a,a,a,a-tetrakis[0-[Nmethylisonicotinamido)phenyl]porphyrin) 5+ and Fe1° (meso-tetrakis[N-methylpyridinium-4-yl]porphyrin)5+ with NC', C02-, and 02", Inorg. Chem. 32:941-947 (1993).
Batinic-Haberle et al., "A novel Synthetic Superoxide Dismutase Mimetic(III) tetrakis (N-ethylpyridinium-2-yl) porphyrin (MnIIITE-2-PyP5) Protects Lungs from Radiation-Induced Injury", International Journal of Radiation Oncology Biology Physics, vol. 51, No. 3 Supplement I, 2001, 235-236 & 43rd Annual Meeting of the American Society for Therapeutic Radiology and Oncology, San Francisco, CA, USA, Nov. 4-8, 2001.
Batinic-Haberle et al., "A Potent Superoxide Dismutase Mimic Manganese[B]-Octabromo-meso-tetrakis-(Nmethylpyridinium-4-yl)Porphyrin", Archives of Biochemistry and Biophysics 343(2):225-233 (1997).
Batinic-Haberle et al., "Manganese(ill) meso-tetrakis(ortho-N-alkylpyridyl)porphyrins. Synthesis, characterization, and catalysis of 02.-dismutation", J. Chem. Soc. Dalton Trans., pp. 2689-2696 (2002).
Batinic-Haberle et al., "Relationship among Redox Potentials, proton Dissociation Constants of Pyrrolic Nitrogens, and in Vivo and in Vitro Superoxide Dismutating Activities of Manganese(III) and Iron(III) Water-Soluble Porphyrins", Inorg. Chem. 38:4011-4022 (1999).
Batinic-Haberle et al., "The Ortho Effect Makes Manganese(III) Meso-Tetrakis-(N-Methylpyridinium-2-yl)Porphyrin a Powerful and Potentially Useful Superoxide Dismutase Mimic", The Journal of Biological Chemistry 273 (38):245214528(1998).
Batinic-Haberle et al., "The Ortho Effect Makes Manganic Meso-Tetrakis-(N-Methylpyridinium-2-YL)(MnTM-2-PyPs+) A Powerful and Useful Superoxide Dismutase Mimic", Oxygen '97, The 4th Annual Meeting of the Oxygen Society, Council Meeting, The Palace Hotel, San Francisco, California, Nov. 20-24, 1997,—p. 38, Abstract 1-8.
Baudry et al., "Salen-Manganese Complexes are Superoxide Dismutase-Mimics", Biochemical and Biophysical Research Communication 192(2):964-968 (1993).
Beckman et al., "Apparent hydroxyl radical production by peroxynitrite: Implications for endothelial injury from nitric oxide and superoxide", Proc. Natl. Acad. Sci. USA 87:1620-1624 (1990).
Bedioui et al., "Metalloporphyrin-Polypyrrole Film Electrode: Characterization and Catalytic Application", J. Electroanal. Chem. 207:87-99 (1986).
Beil Winfried et al., "Helicobacter pylori Reduces Intracellular Glutathione in Gastric Epithelial Cells", Digestive Diseases and Sciences 45(9):1769-1773 (2000).
Berezin et al., "Effect of ligand structure on the kinetic stability of tetraphenylporphyrin complexes of zinc and cadmium", Zhurnal Neorganicheskoi Khimii 25(10):2645-2652 (1980)—English Abstract.
Berezin et al., "Factors determining the stability of complexes of copper with p-substituted derivatives of tetraphenylporphine", Zhurnal Fizicheskoi Khimil 53(11):2716-2719 (1979)—English Abstract.
Beyer, Jr., Characterization of a Superoxide Dismutase Mimic Prepared from Desferrioxamine and Mn02, Archives of Biochemistry and Biophysics 271(1):149-156 (1989).
Bishop et al., "The Reaction of Thiomides with Phosphorus Ylides", J. Org. Chem. 56:5079-5091 (1991).
Bloodsworth et al., "Manganese-Porphyrin Reactions with Lipids and Lipoproteins", Free Radical Biology & Medicine 28(7):1017-1029 (2000).

Bockhorst and Hoehn-Berlage, "An Optimized Synthesis of Manganese meso-Tetra(4-sulfonato phenyl) porphine: A Tumor-Selective MRI Contrast Agent", Tetrahedron 50(29):8657-8660 (1994).
Boissinot et al., "Rational Design and Expression of a Heparin-Targeted Human Superoxide Dismutase", Biochemical and Biophysical Research Communication 190(1):250-256 (1993).
Bors et al., "An expanded function for superoxide dismutase", Chemical Abstracts 115:388 (1991), Abstract No. 109185h.
Brigelius et al., "Superoxide Dismutase Activity of Low Molecular Weight Cu2+-Chelates Studied by Pulse Radiolysis", FEBS Letters 47(1):72-75 (1974).
Burke, "Photochemical and thermal transformations of phytochrome", Chem. Physiol. Bile Pigm., Int. Symp., pp. 509-517 (1975).
Butje et al., "Electronic Spectra, Resonance Raman Spectra and Solution Properties of Water-soluble (Cu(II), Ni(II) and Co(III) Porphyrins", Inorg. Chim. Acta 167:97-108 (1990).
Callot and Schaeffer, "Ring contraction of homoporphyrins to porphyrins, meso-Reactivity of 5,10,15Triphenylporphin and Porphin", J. Chem. Research (S):51 (1978).
Chung et al., "Protective effects of hemin and tetrakis(4-benzoic acid)porphyrin on bacterial mutagenesis and mouse skin carcinogenesis induced by 7,12-dimethylbenz[a]anthracene", Mutation Research 472:139-145 (2000).
Clyde et al., "Distribution of Manganese Superoxide Dismutase mRNA in Normal and Hyperoxic Rat Lung", American Journal of Respiratory Cell and Molecular Biology 8:530-537 (1993).
Collman et al., "Synthesis of "Face to Face" Porphyrin Dimers Linked by 5,15-Substituents: Potential Binuclear Multielectron Redox Catalysts", J. Am. Chem. Soc. 103:516-533 (1981).
Comhair et al., "Rapid loss of superoxide dismutase activity during antigen-induced asthmatic response", Lancet 355 (9204):624 (2000).
Crapo and Tierney "Superoxide dismutase and pulmonary oxygen toxicity", Am. J. Physiol. 226:1401-1407 (1974).
Crapo et al., "Superoxide Dismutase and Oxygen Toxicity", Clinical Research, p. 222, 1975.
Crapo et al., "The Failure of Aerosolized Superoxide Dismutase to Modify Pulmonary Oxygen Toxicity", American Review of Respiratory Disease 115:1027-1033 (1977).
Crapo et al., 721195, Document No. 123:218443 (1995).
Darr et al., "A Mimic of Superoxide Dismutase Activity Based Upon Desferrioxamine B and Manganese(IV)", Archives of Biochemistry and Biophysics 258(2):351-355 (1987).
Datta-Gupta et al., "Synthetic Porphyrins II Preparation and Spectra of Some Metal Chelates of para", Journal of Substituted-mesa-TetraDhenylporphines, J. of Pharmaceutical Science 57(2):300-304 (1968).
Datta-Gupta et al., "Synthetic Porphyrins. I. Synthesis and Spectra of Some para-Substituted mesoTetraphenylporphines (1)", J. Heterocycl. Chem. 3:495-502 (1966).
Davila et al., "Sterically-Hindered Zinc Porphyrins for Solar-Energy Conversion", J. Chem. Soc., Chem. Commun., pp. 525-527 (1987).
Day et al., "A Metalloporphyrin Superoxide Dismutase Mimetic Protects Against Paraquat-Induced Endothelial Cell . Injury, in Vitro", The Journal of Pharmacology and Experimental Therapeutics 275(3):1227-1232 (1995).
Day et al., "Manganic Porphyrins Possess Catalase Activity . . . ," Arch. Biochem. Biophys., vol. 347, No. 2, pp. 256-262 (1997).
Day, "Catalytic Antioxidants: a Radical Approach to new Therapeutics," DDT vol. 9, No. 13, pp. 557-566 (Jul. 2004), www.drugdiscoverytoday.com, therapeutic focus, reviews.
De Peretti et al., "Imidazol[2,1-b]benzoxazole-3-acetamide derivatives, their preparation, and their therapeutic use", Chemical Abstracts 121:1016, Abstract No. 121:200896u.
Dealvare et al., "Mechanism of Superoxide Anion Scavenging Reaction by Bis-(Salicylato)-Copper(II) Complex", Biochemical and Biophysical Research Communications 69(3):687-694 (1976).
Deune et al., "Prevention of Ischemia-Reperfusion Injury with a Synthetic Metalloprotein Superoxide Dismutase Mimic, SC52608", Plastic and Reconstructive Surgery 98(4):711-718 (1996).
DiGuiseppi et al., "Putative Superoxide Dismutase Activity of Iron-EDTA: A Reexamination", Archives of Biochemistry and Biophysics 203(1):145-150 (1980).

* cited by examiner

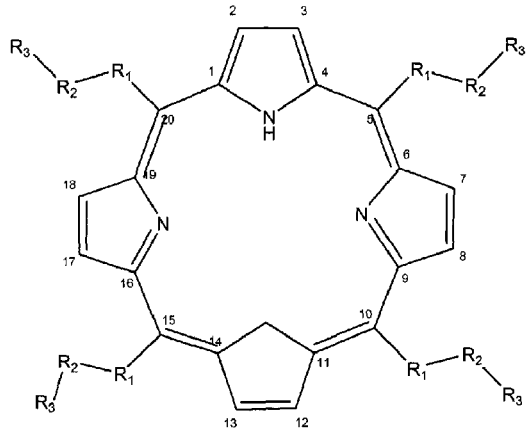

or a pharmaceutically acceptable salt thereof, wherein $R_1$ is a bond 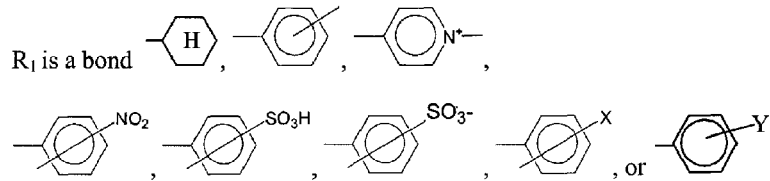

wherein X is a halogen and Y is an alkyl group and wherein  indicates bonding to $R_2$ at any position and

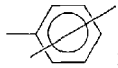 indicates bonding to $R_2$ and the substituent at any position; and $R_2$ is a bond, $-(CY'_2)_n-$, $-(CY'_2-CY'=CY')_n-$, $-(CY'_2-CY'_2-CH=CH)_n-$, $-(CY'=CY')_n-$, or $-(CY'_2-C(O))_n-$, wherein Y' is hydrogen or an alkyl group and wherein n is 1 to 8; and $R_3$ is -Y''', -OH, -NH$_2$, -N$^+$(Y'')$_3$, -COOH, -COO$^-$, -SO$_3$H, -SO$_3^-$, -C-PO$_3$H$_2$ or -CPO$_3$H$^-$, wherein Y'' is an alkyl group.

Fig. 1A

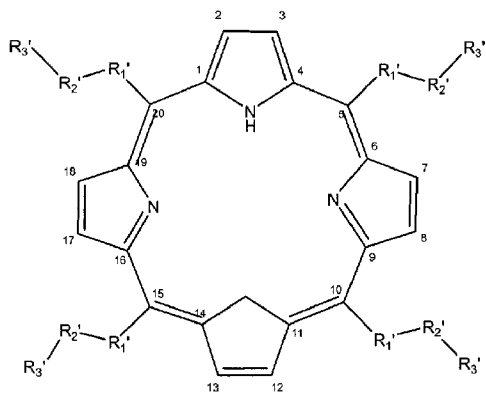

or a pharmaceutically acceptable salt thereof, wherein each $R_1$ is independently a bond, 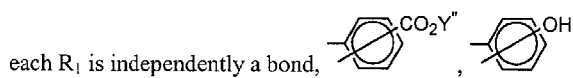

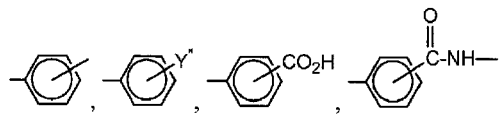

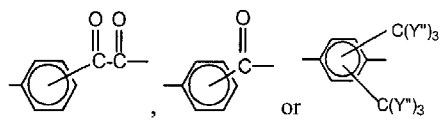

wherein Y" is an alkyl group, and wherein [phenyl]

indicates bonding to $R_2'$, at any position and [phenyl]

indicates bonding to $R_2'$ and the $R_1'$ phenyl substituent at any position;

each $R_2'$ is independently a bond, or $-(CH_2)_n-$ wherein n is 1-4, each $R_3'$ is independently $-Y''$, $-Y'''$, $-H$, $-OH$, $-OY''$, $-NO_2$, $-CN$, $-NH_2$, $-COOH$, $-COY''$, $-COO^-$, or a heterocytyclic group, wherein Y" is as defined above and Y''' is a primary, secondary, tertiary or quaternary amine.

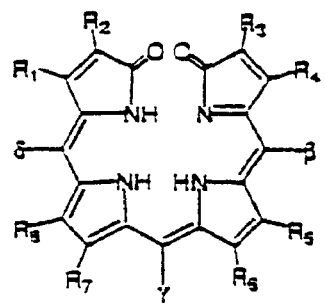

I

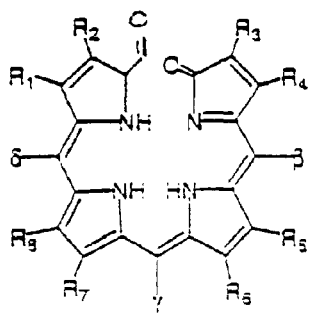

II $R_1$ through $R_8$ are, independently, -H, alkyl, 2-hydroxyalkyl, methoxyalkyl, halogen, nitro, cyano, trialkylammonium, formyl, amide of carboxylic acid, alkyl ester of carboxylic acid, carboxylic acid, glucuronyl or glyceryl ester of carboxylic acid, 1,2-dihydroxyalkyl, acetyl, vinyl, glycosyl or, taurate, and $\beta$, $\gamma$ and $\delta$ are, independently, -H, acetyl, glycyl, benzoate, phenylsulfonate, 2-, or 3-, or 4-N-alkyl-pyridyl, nitrophenyl, halophenyl, methoxyalkyl, halogen, nitro, cyano, trialkylammonium, formyl, amide of carboxylic acid.

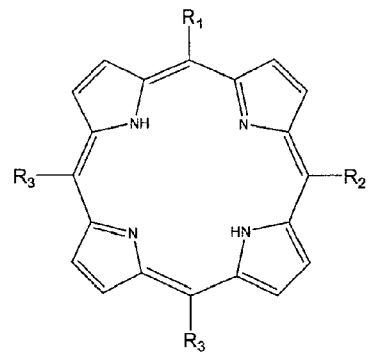
or pharmaceutically acceptable salt thereof
wherein: $R_1$ and $R_2$ are the same and are:
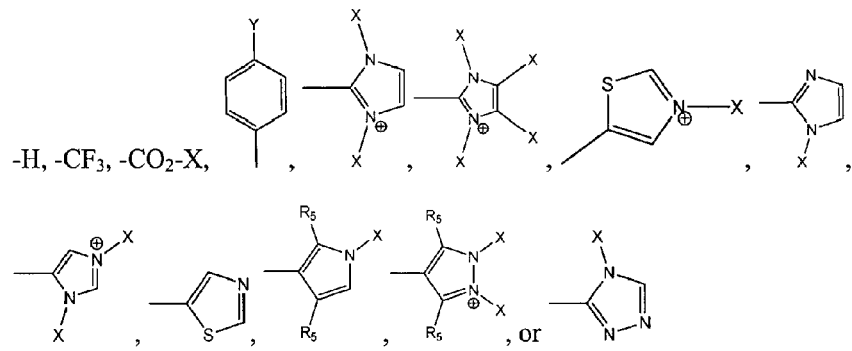
$R_2$ and $R_4$ are the same and are:
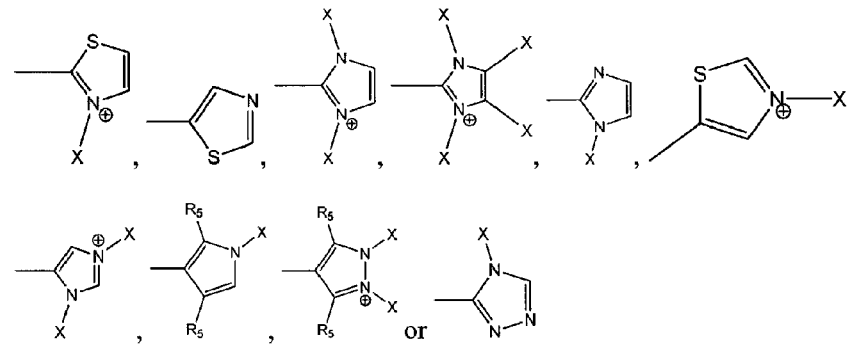
Y is halogen or $-CO_2X$,
each X is the same or different and is an alkyl and each $R_5$ is the same or different (preferably the same) and is H or alkyl.
Fig. 1E

Fig 1F

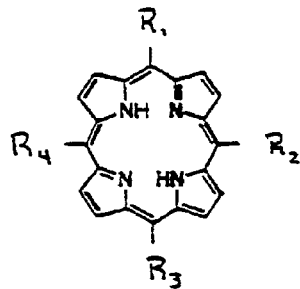

or pharmaceutically acceptable salt thereof wherein:

$R_1$ and $R_3$ are, independently:

-$CO_2C_{1-4}$ alkyl; or

-$CO_2(CH_2)_nCX_3$, wherein X is halogen and n = 1 to 3;

$R_2$ is:

-H

-$C_{1-4}$ alkyl

-COOH

-$CO_2C_{1-4}$ alkyl,

-$CO_2(CH_2)_nCX_3$, wherein X is halogen and n = 1 to 3,

-$CON(CH_3)_2$, or

-$CX_3$, wherein X is halogen; and $R_4$ is:

-H,

-$C_{1-4}$ alkyl

-COOH,

-$CO_2C_{1-4}$ alkyl,

-$CO_2(CH_2)_nCX_3$, wherein X is halogen and n = 1 to 3,

-$CON(CH_3)_2$, or

-$CX_3$, wherein X is halogen.

I          or          II, or pharmaceutically acceptable salt thereof,
   wherein
       each R is, independently, a $C_1$-$C_8$ alkyl group,
   and
       each P is, independently, an electron withdrawing group or hydrogen.

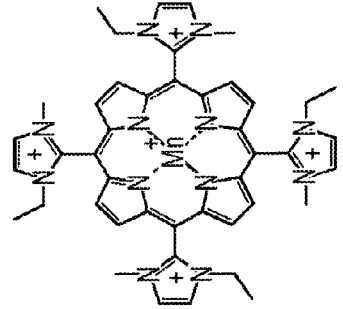
10151
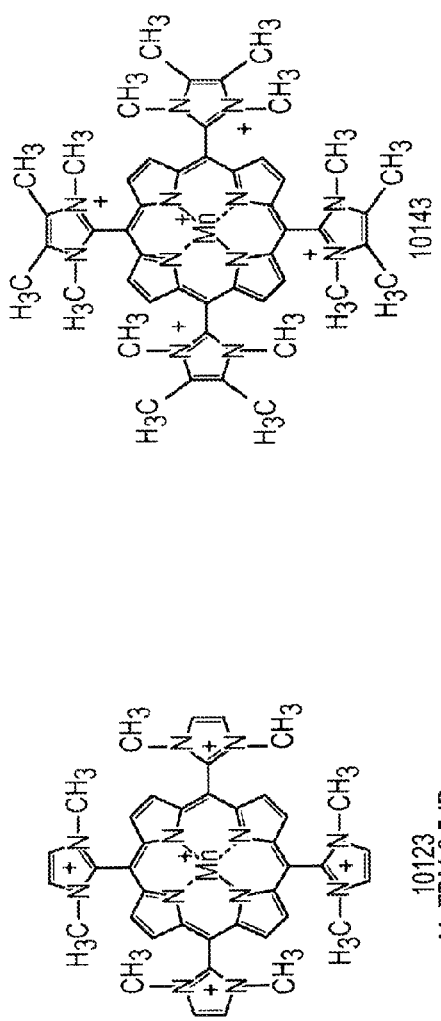
10143
10123
MnTDM-2,5-IP
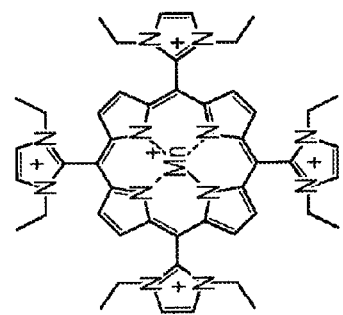
10150
MnTDE-2,5-IP
FIG. 1H Continued Catalytic Antioxidant Metalloporphyrin
[MnTBAP]

Figure 9
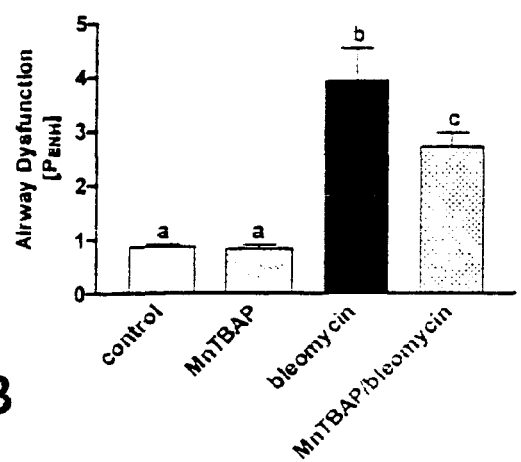
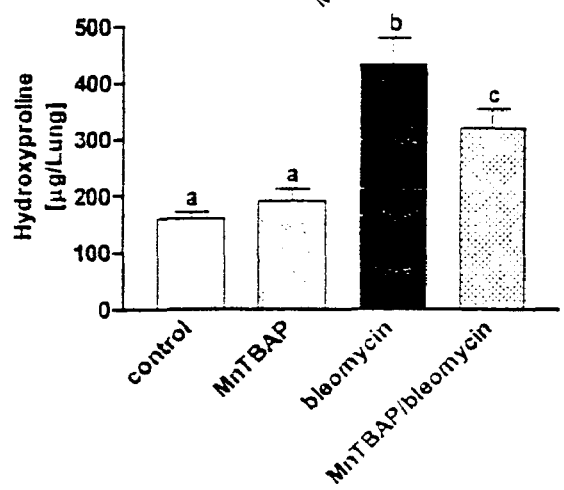

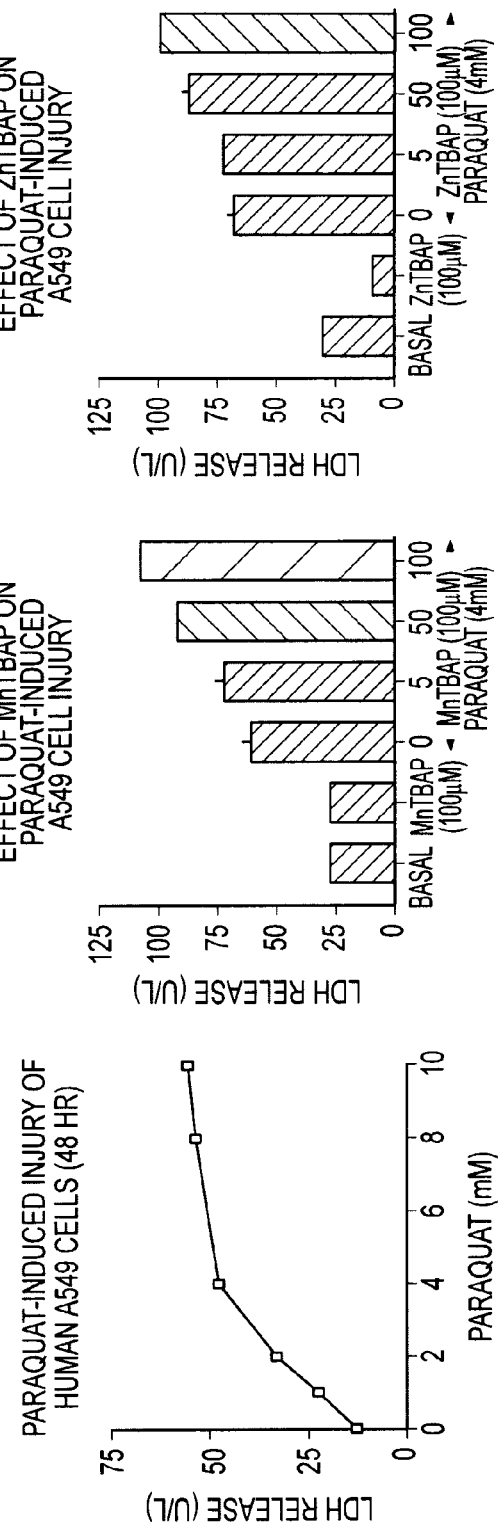

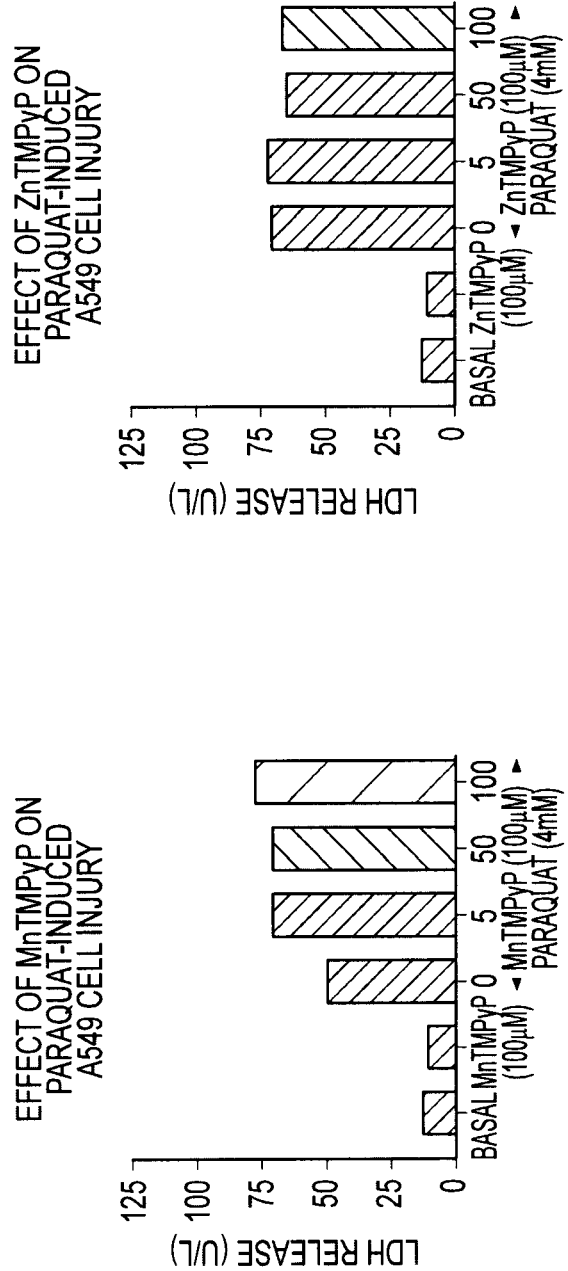

INC-01 Blinded Mucositis Scores

CANCER THERAPY

RELATED APPLICATIONS

This application is a divisional of U.S. patent application Ser. No. 10/051,367, filed Jan. 22, 2002, which claims priority from Provisional Application No. 60/262,390, filed Jan. 19, 2001, the entire disclosures of which are hereby incorporated by reference in their entirety for all purposes.

TECHNICAL FIELD

The present invention relates, in general, to cancer therapy, and, in particular, to a method of preventing or treating cancer using low molecular weight antioxidants (e.g., mimetics of superoxide dismutase (SOD)) as the active agent or as a chemo- and/or radio-protectant. The invention also relates to compounds and compositions suitable for use in such a method.

BACKGROUND

Oxidants are produced as part of the normal metabolism of all cells but also are an important component of the pathogenesis of many disease processes. Reactive oxygen species, for example, are critical elements of the pathogenesis of diseases of the lung, the cardiovascular system, the gastrointestinal system, the central nervous system and skeletal muscle. Oxygen free radicals also play a role in modulating the effects of nitric oxide (NO.). In this context, they contribute to the pathogenesis of vascular disorders, inflammatory diseases and the aging process.

A critical balance of defensive enzymes against oxidants is required to maintain normal cell and organ function. Superoxide dismutases (SODs) are a family of metalloenzymes that catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione peroxidase. While extracellular fluids and the extracellular matrix contain only small amounts of these enzymes, other extracellular antioxidants are also known to be present, including radical scavengers and inhibitors of lipid peroxidation, such as ascorbic acid, uric acid, and α-tocopherol (Halliwell et al, Arch. Biochem. Biophys. 280:1 (1990)).

The present invention provides methods of cancer prevention and therapy that involve the use of low molecular weight mimetics of SOD.

SUMMARY OF THE INVENTION

The present invention relates to a method of modulating intra- or extracellular levels of oxidants. In one embodiment, the invention relates to a method of protecting normal tissue of a cancer patient from the toxic effects associated with gene therapy, immunotherapy, chemotherapy and/or radiation therapy using mimetics of SOD. In a further embodiment, the invention relates to a method of preventing or treating cancer in a patient in need of such treatment using low molecular weight antioxidants. The invention additionally relates to agents suitable for use in such methods, including methine (ie, meso) substituted porphyrins and tetrapyrroles.

Objects and advantages of the present invention will be clear from the description that follows.

BRIEF DESCRIPTION OF THE DRAWING

FIGS. 1A-1H show the structures of certain generic and specific definitions of compounds suitable for use in the present invention. With reference to FIG. 1C, mimetics of the invention can be of Formula I or Formula II, or dimeric forms thereof, an example of a dimeric form being shown in FIG. 1D. With reference to FIG. 1H, the SOD activities of certain of the depicted compounds are shown in Table 1 (as measured by the cytochrome C method):

TABLE 1

| Compound | SOD activity (U/mg) |
| --- | --- |
| 10110 | 225 |
| 10113 | 10,648 |
| 10123 | 17,061 |
| 10143 | 14,038 |
| 10150 | 14,789 |
| 10153 | 23,467 |
| 10158 | 14,342 |
| CuZn-SOD | 2,200 |

Figure 1D:
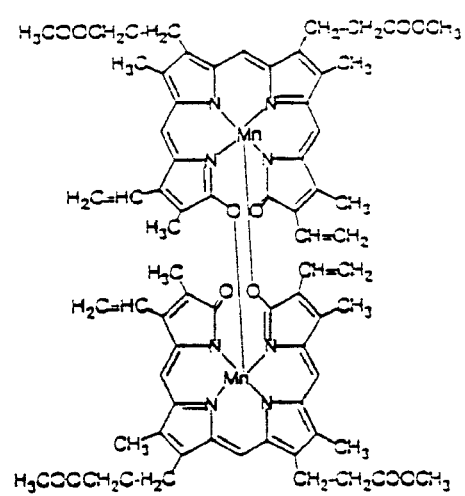
Figure 1G:
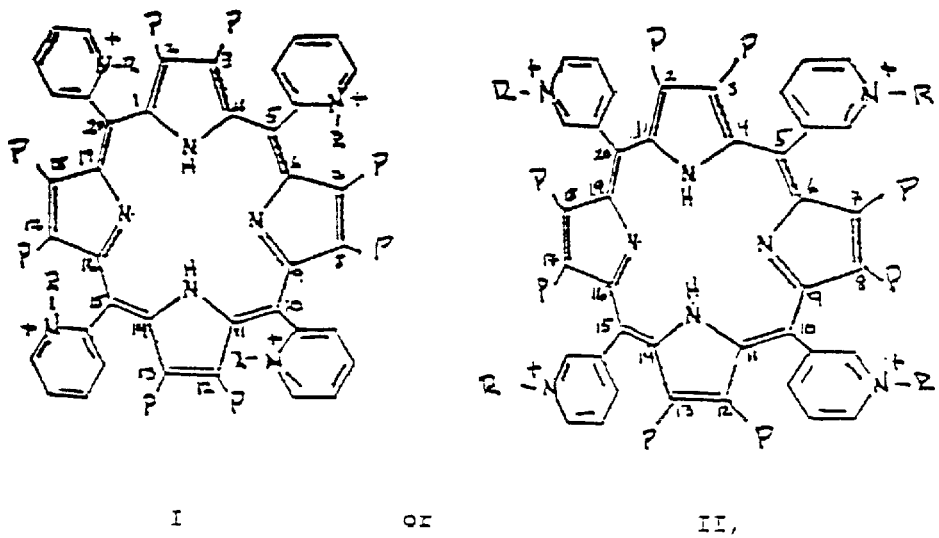
Figure 1H:
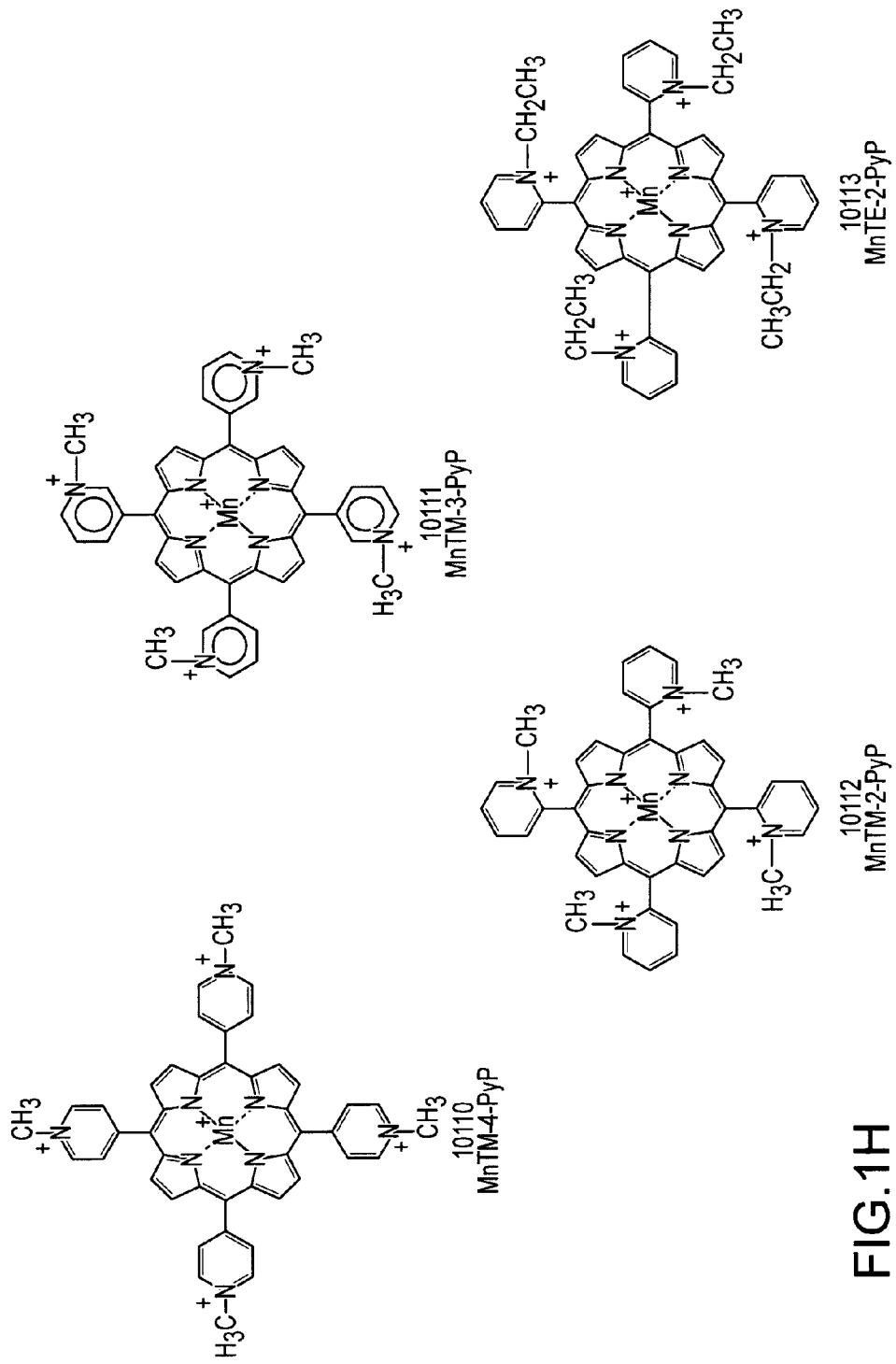
Figure 1H:
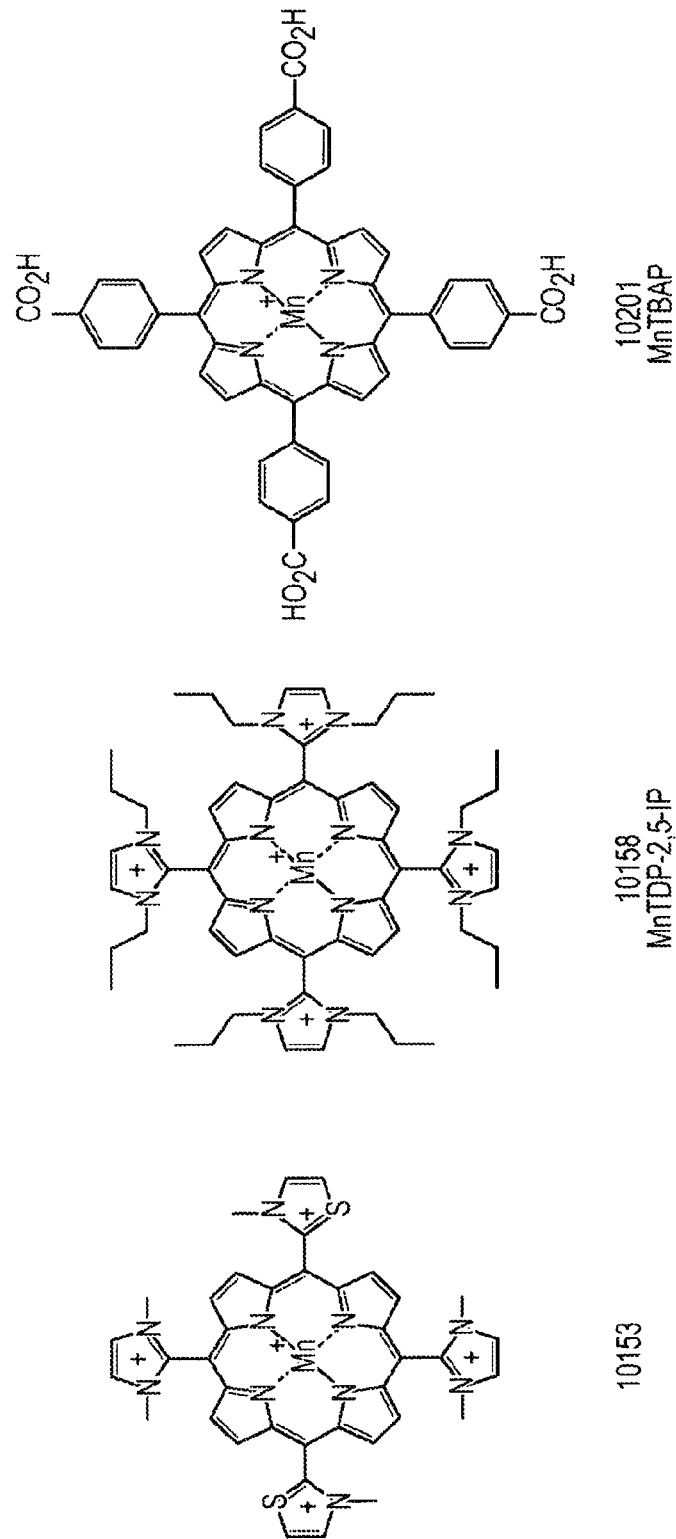
Figure 2A:
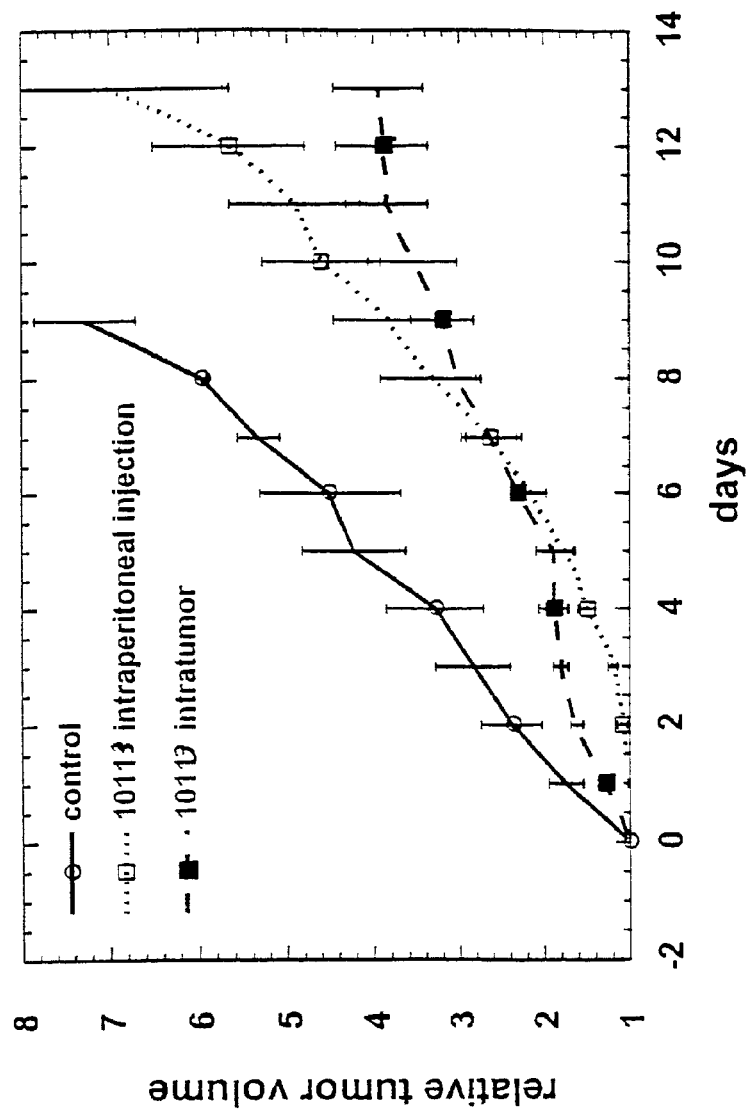
Figure 2B:
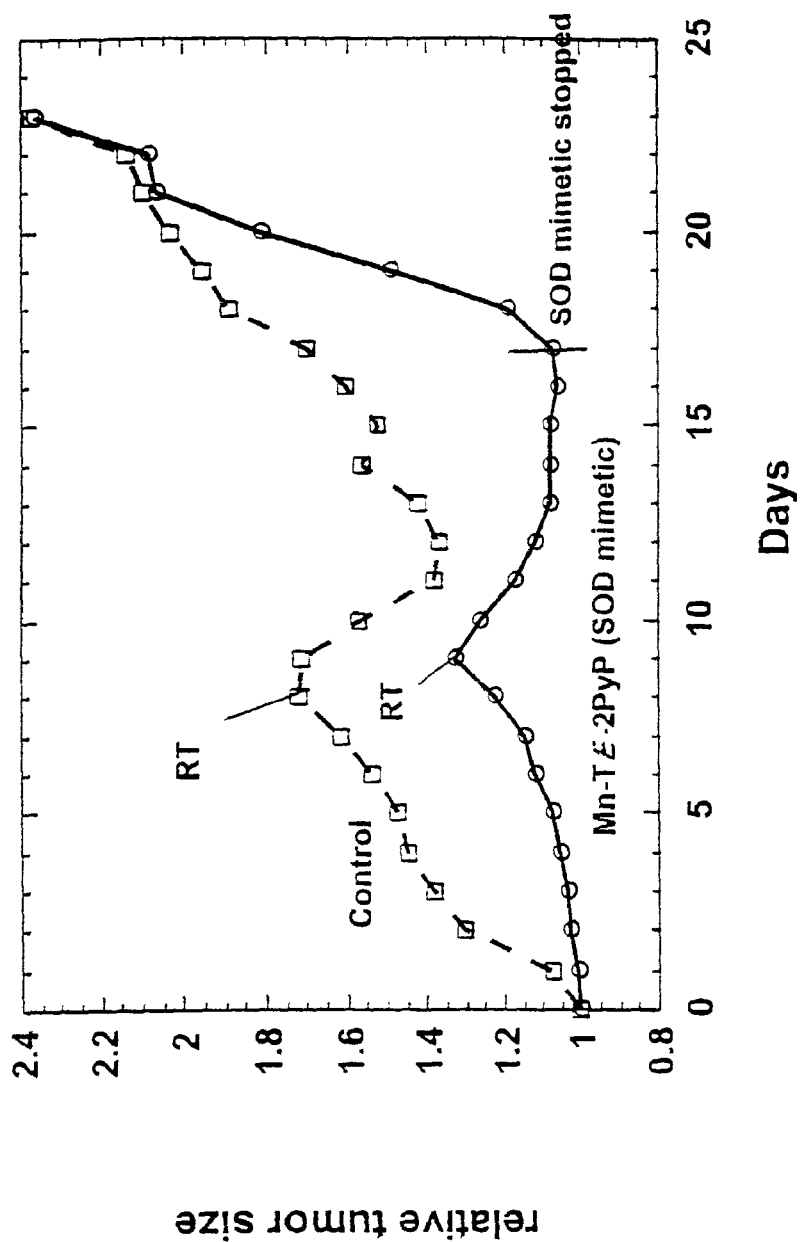
Figure 2C:
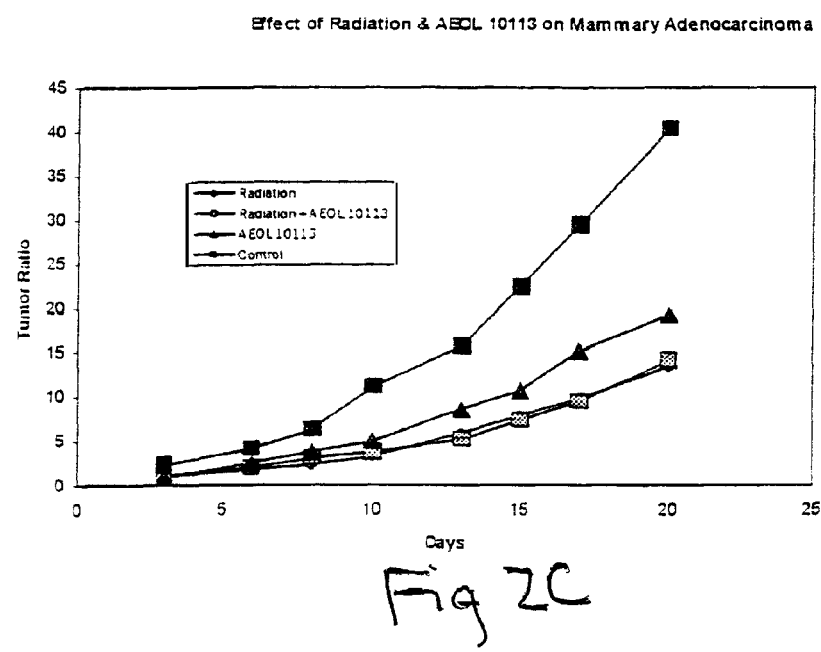

FIGS. 2A-2C. (FIG. 2A) B16 melanoma tumor treated with SOD mimetic. The mimetic was 10113 at a dose of 6 mg/kg given intraperitoneally qd for 5 days. (FIG. 2B) Mammary adenocarcinoma treated with SOD mimetic. 10113 was given intraperitoneally at a dose of 6 mg/kg/day for 16 days. Radiation therapy (RT), 21 Gy, was given on day 8 or 9. (FIG. 2C) Fischer 344 rats with subcutaneously implanted R3230 AC mammary adenocarcinomas received Radiation treatment (21 Gy Day 1), AEOL 10113 (6 mg/kg/day IP Day 1 to 20), the combination Radiation and AEOL 10113 (as above), or Control treatment. All 3 treatments significantly (p<0.05) inhibited tumor growth as compared to control as measured by Day 20 Tumor Ratio and Days for 5-fold tumor growth but did not differ from each other.

Figure 3:
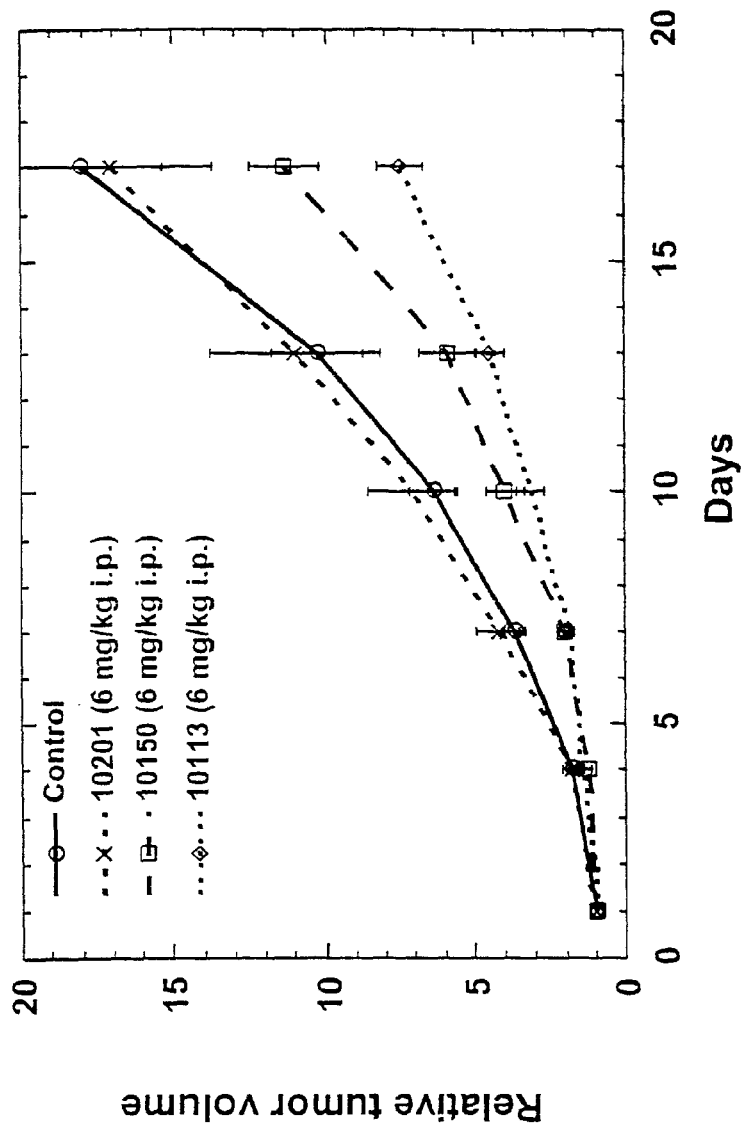

FIG. 3. Tumor growth inhibition using tumor growth delay assay in Fisher 344 rats after intraperitoneal administration of 6 mg/kg of three different compounds.

Figure 4:
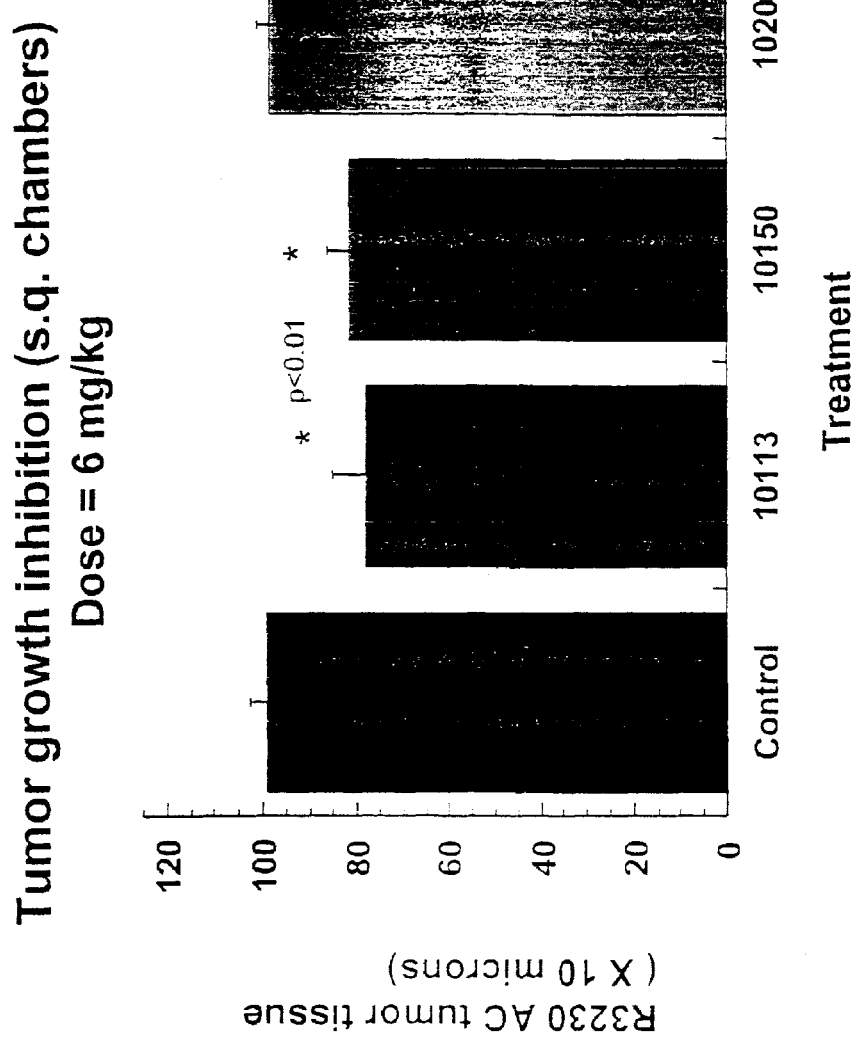

FIG. 4. Animals were pretreated with different SOD mimetics (6 mg/kg i.p.) 24 hours before implantation of 2.5 mil./ml R3230 mammary adenocarcinoma cells in Z-chambers. Significant (p<0.01) inhibition of tumor development was observed in animals treated with 10113 (manganese(III) tetrakis(N-ethylpyridinium-2-yl)porphyrin) and 10150 (manganese(III)tetrakis(N-diethylimidazolium-2,5-yl)porphyrin) compounds.

Figure 5:
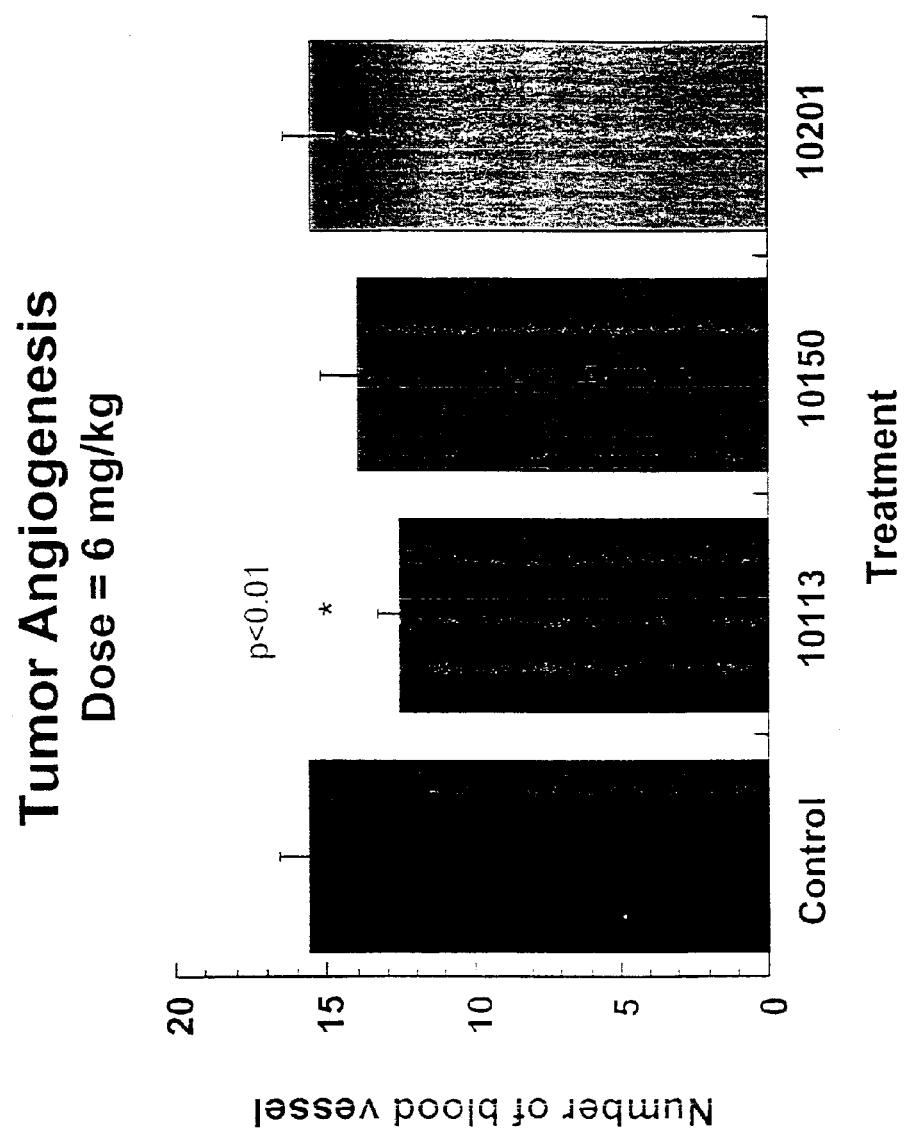

FIG. 5. Antiangiogenesis: Animals were pretreated with different SOD mimetics (6 mg/kg i.p.) 24 hours before implantation of 2.5 mil./ml R230 mammary adenocarcinoma cells in Z-chambers. Significant inhibition of tumor angiogenesis was observed in animals treated with 10113 compound.

Figure 6:
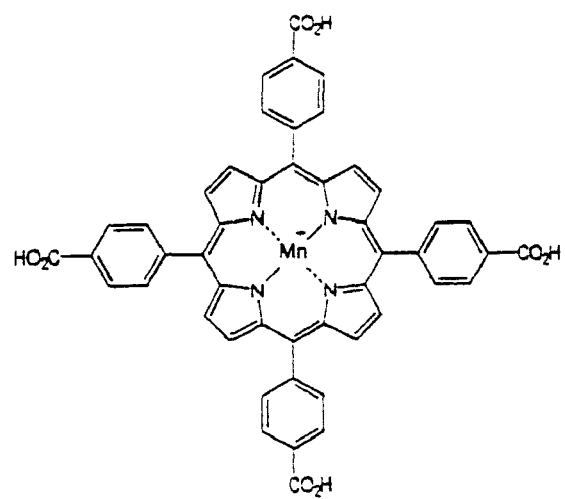

FIG. 6 shows the chemical structure of a catalytic antioxidant, manganese (III) tetrakis (4-benzoic acid) porphyrin (MnTBAP).

Figure 7:
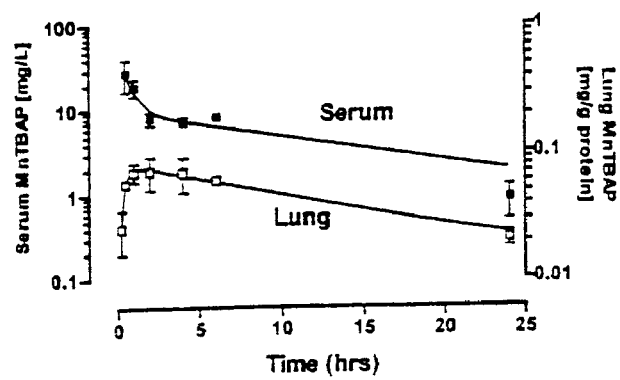

FIG. 7 shows the pharmacokinetic profile of MnTBAP in mice given a single 10 mg/kg, ip dose. MnTBAP levels in serum (closed squares) and lung tissue (open squares) were measured at 0.3, 0.5, 1, 2, 4, 6 and 24 hours after drug treatment. Results are the means of 3 mice±SEM. Data were calculated from curve-fitted data assuming a two-compartment pharmacokinetic model. MnTBAP rapidly equilibrated into the blood stream and the lungs of mice.

Figure 8:
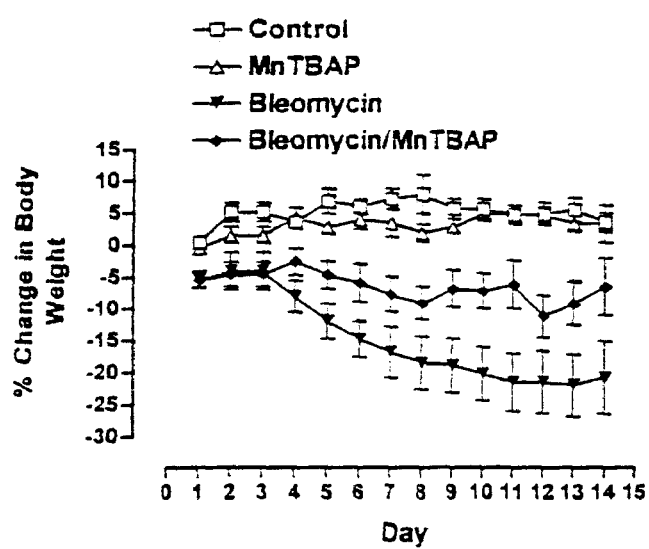

FIG. 8 shows that MnTBAP attenuates bleomycin-induced weight loss in mice. Control (phosphate buffered saline 1 ml/kg, ip, twice daily; open square) and MnTBAP (5 mg/kg, ip, twice daily; open triangle) treated mice had similar weight changes throughout the study period. Bleomycin (closed triangle) treated mice had significantly more weight loss than control mice and this was attenuated in the bleomycin plus MnTBAP (closed diamond) treated mice after 5 days of treatment and continued to the end of the study. Results are the means of 5 mice±SEM.

FIGS. 9A and 9B show that MnTBAP attenuates bleomycin-induced airway constriction and collagen accumulation. FIG. 9A. Whole body barometric plethysmography was employed and enhanced pause ($P_{ENH}$) was used as a non-invasive index of airway dysfunction. Control (phosphate buffered saline, 1 ml/kg, ip, twice daily; open bar) and MnTBAP (5 mg/kg, ip, twice daily; hatched bar) treated mice had similar $P_{ENH}$ values after 14 days of treatment. Bleomycin (closed bar) treated mice had significantly elevated $P_{ENH}$ values compared to control mice and this was attenuated in the bleomycin plus MnTBAP (crosshatched bar) treated mice. FIG. 9B. Lung fibrosis was biochemically assessed using hydroxyproline as an index of collagen accumulation. Control and MnTBAP treated mice had similar hydroxyproline values after 14 days of treatment. Bleomycin treated mice had significantly elevated hydroxyproline values compared to control mice and this was attenuated in the bleomycin plus MnTBAP treated mice. Results are the means of 5 mice±SEM. Bars with different letters are significantly different from one another, $p<0.05$.

Figure 10:
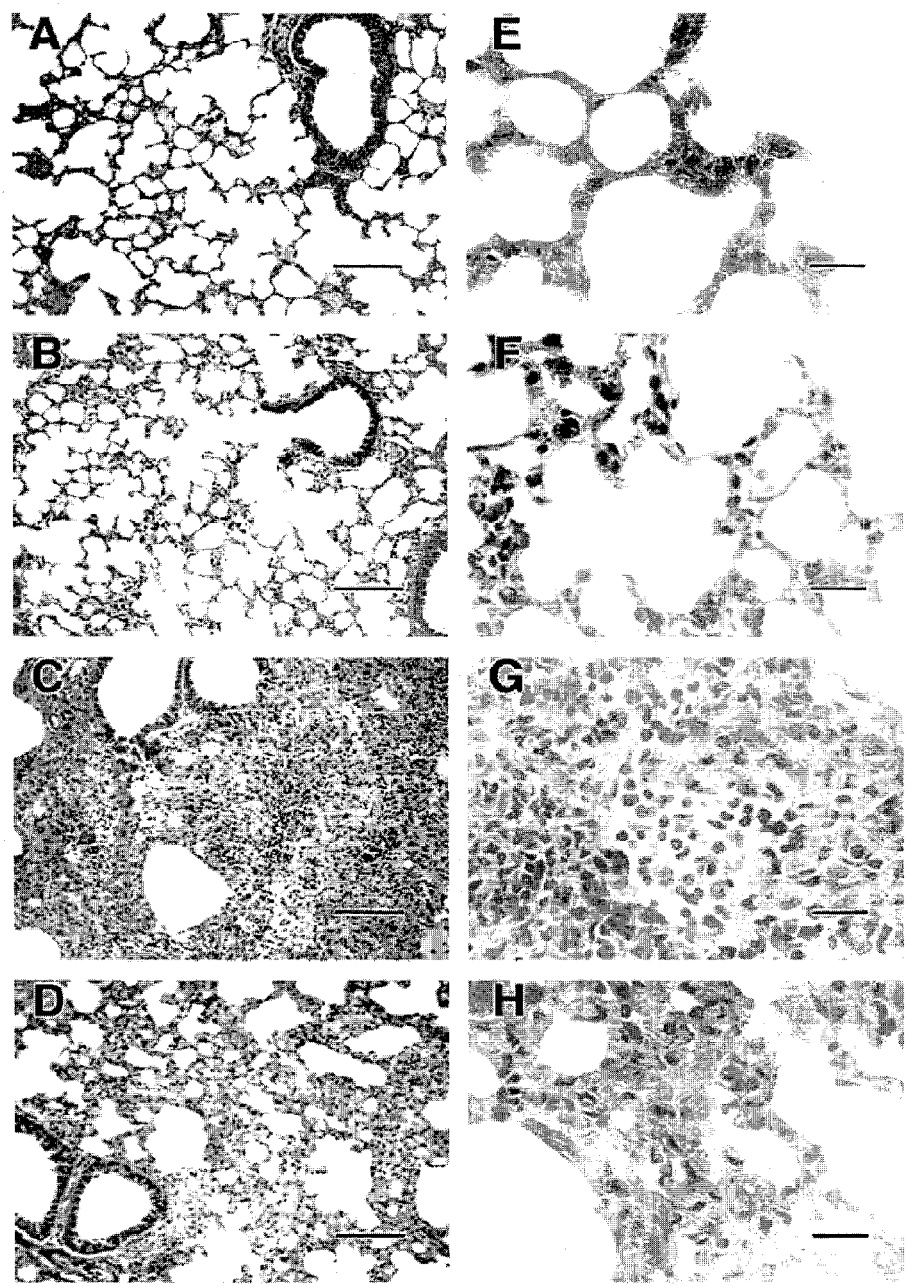

FIGS. 10A-10H show that MnTBAP attenuates bleomycin-induced pulmonary injury. Mice were treated with phosphate buffered saline (PBS, 1 ml/kg, ip, twice daily for 14 days), MnTBAP (5 mg/kg, ip, twice daily for 14 days, bleomycin (3.5 U/kg, it, once) or bleomycin plus MnTBAP and killed after 14 days. Lungs were inflation fixed in 10% neutral buffered formalin. Five-micron thick sections were stained with hematoxylin and eosin and examined microscopically. FIG. 10A. Representative lung section from a PBS/PBS treated mouse. FIG. 10B. Representative lung section from a PBS/MnTBAP treated mouse. FIG. 10C. Representative lung section from a bleomycin/PBS treated mouse. FIG. 10D. Representative lung section from a bleomycin/MnTBAP treated mouse. Bar represents 100 microns. Five-micron thick sections were stained with Masson trichrome and examined microscopically. FIG. 10E. Representative lung section from a bleomycin/PBS treated mouse. FIG. 10F. Representative lung section from a bleomycin/MnTBAP treated mouse. FIG. 10G. Representative lung section from a PBS/PBS treated mouse. FIG. 10H. Representative lung section from a PBS/MnTBAP treated mouse. Bar represents 20 microns.

Figure 11:
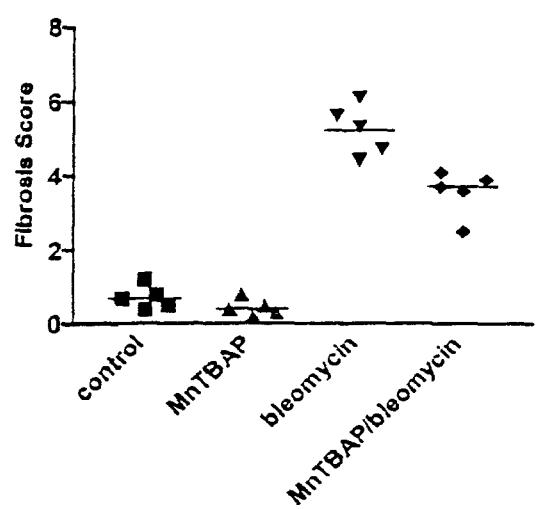

FIG. 11. MnTBAP attenuates bleomycin-induced lung injury as determined by histopathologic analysis. Mice were treated with either bleomycin (3.5 U/kg, it) or phosphate buffered saline (PBS, 50 µl) and then given MnTBAP (5 mg/kg, ip, twice daily) or PBS (1 ml/kg, ip, twice daily) for 14 days. Lungs were inflation fixed in 10% neutral buffered formalin. Five-micron thick sections were stained with hematoxylin and eosin or Masson Trichrome and examined microscopically. Slides were systematically scanned in a microscope using a X10 objective. Each successive field was individually assessed for severity of interstitial fibrosis and allotted a score between 0 and 8 using a predetermined scale of severity. Scores from the fields were averaged to obtain a pathologic score for each animal. Bars with asterisks are statistically different from the PBS/PBS group ($p<0.05$). A dagger indicates a significant interaction between MnTBAP and bleomycin ($p<0.05$).

Figure 12:
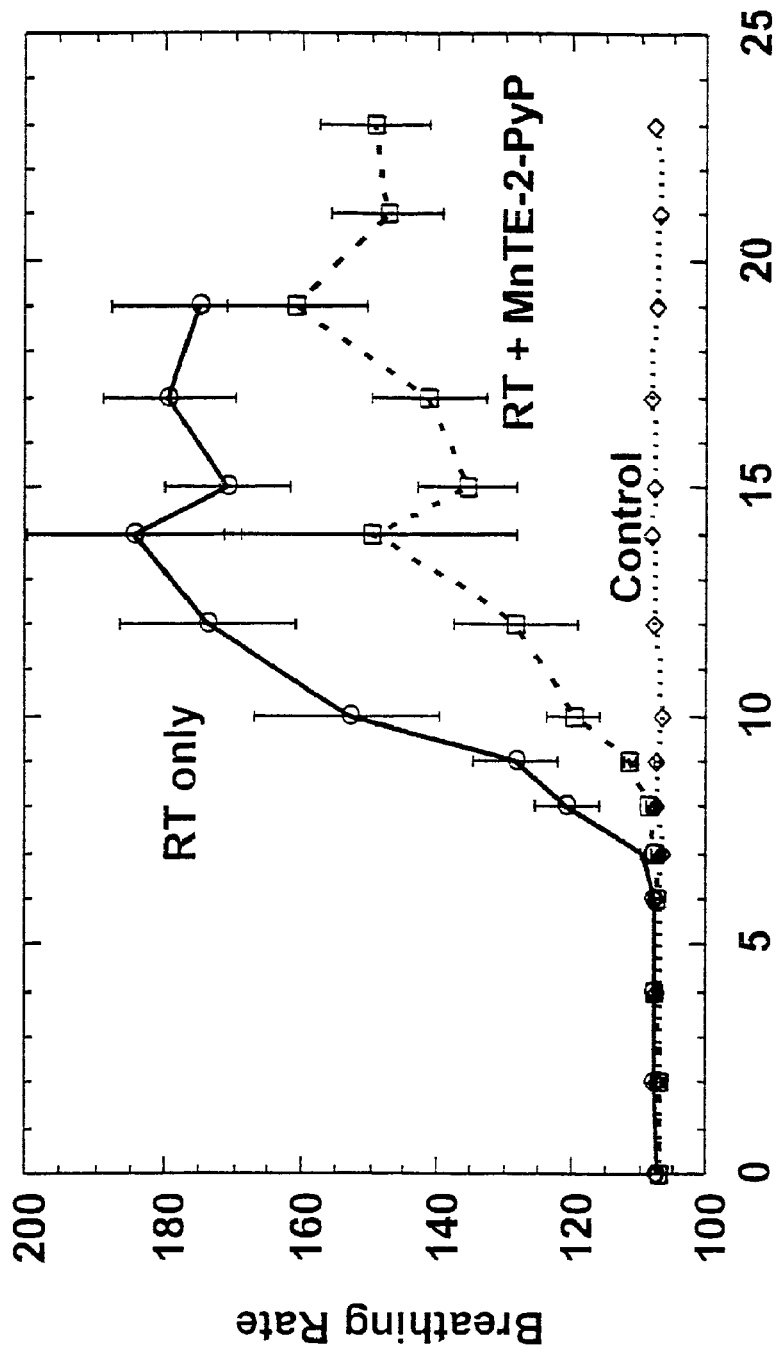

FIG. 12. Changes in breathing rates over 6 months after 28 Gy of right hemithoracic irradiation with and without MnTE-2-PyP (AEOL 10113) (LOCF data set) vs. Control (no radiation).

Figure 13A:
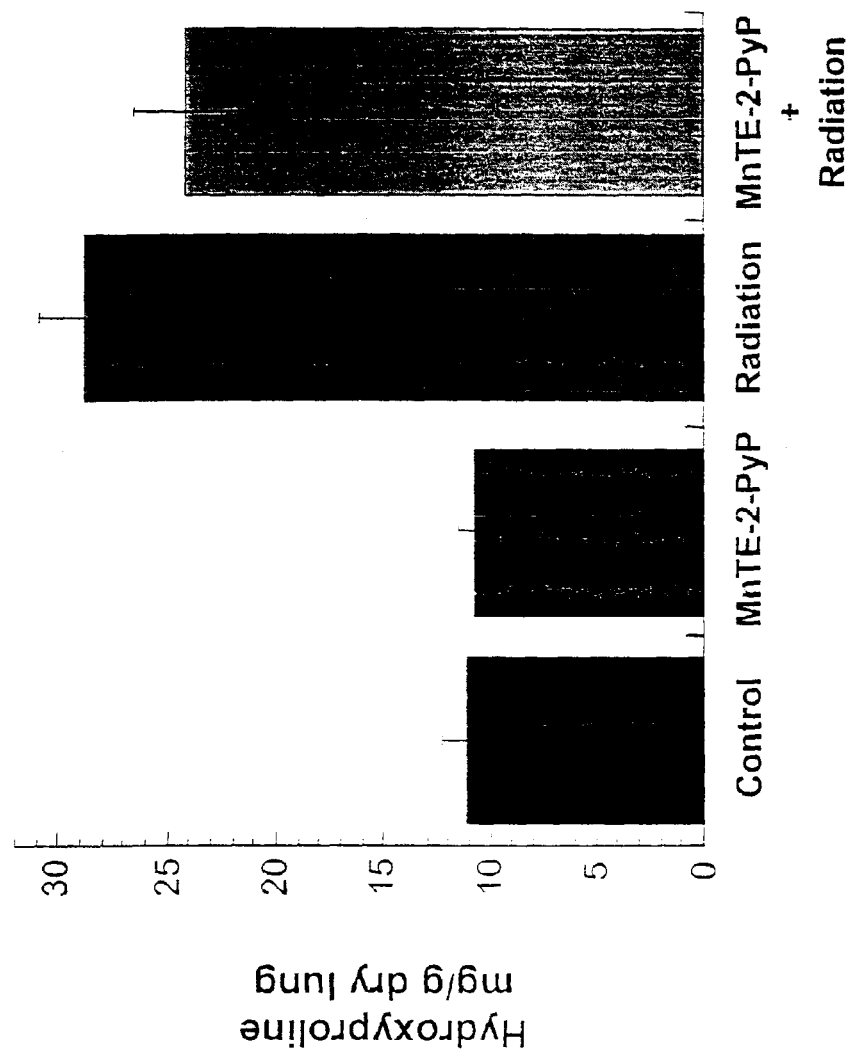
Figure 13B:
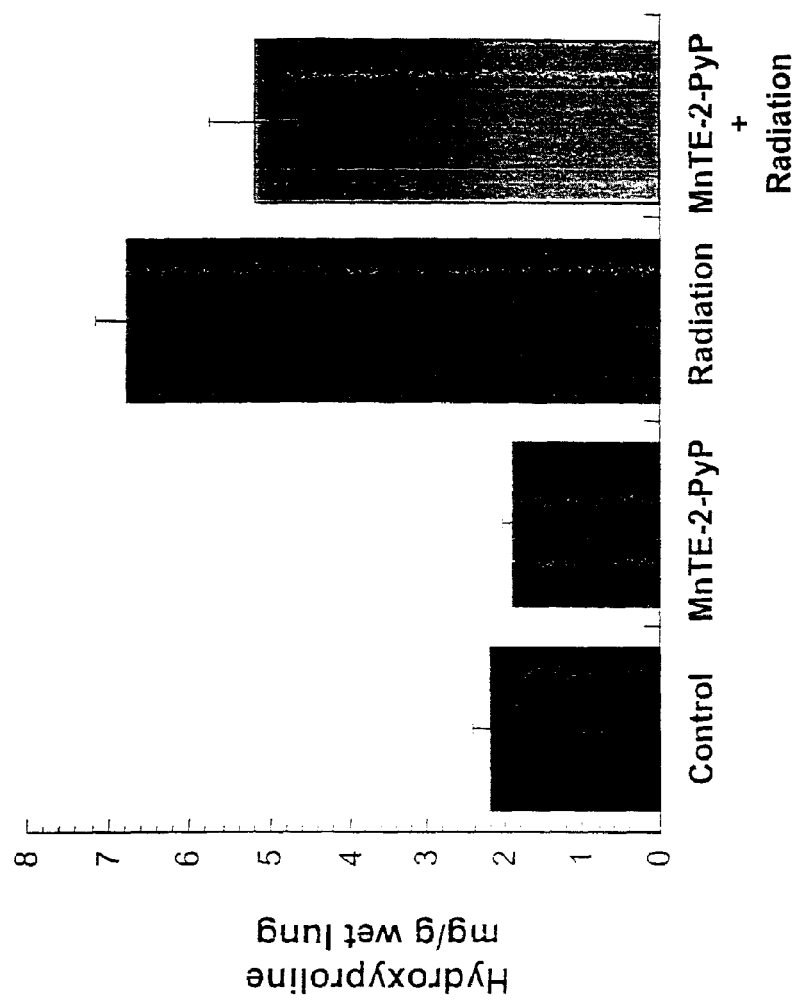

FIGS. 13A and 13B. (FIG. 13A) Assessment of post radiation lung fibrosis. Hydroxy-proline content of upper right lung lobe per gram of wet lung 6 months after 28 Gy of right hemithoracic irradiation. (FIG. 13B) Fibrosis score from histopathology. Results are means of 5 rats±SEM.

Figure 14:
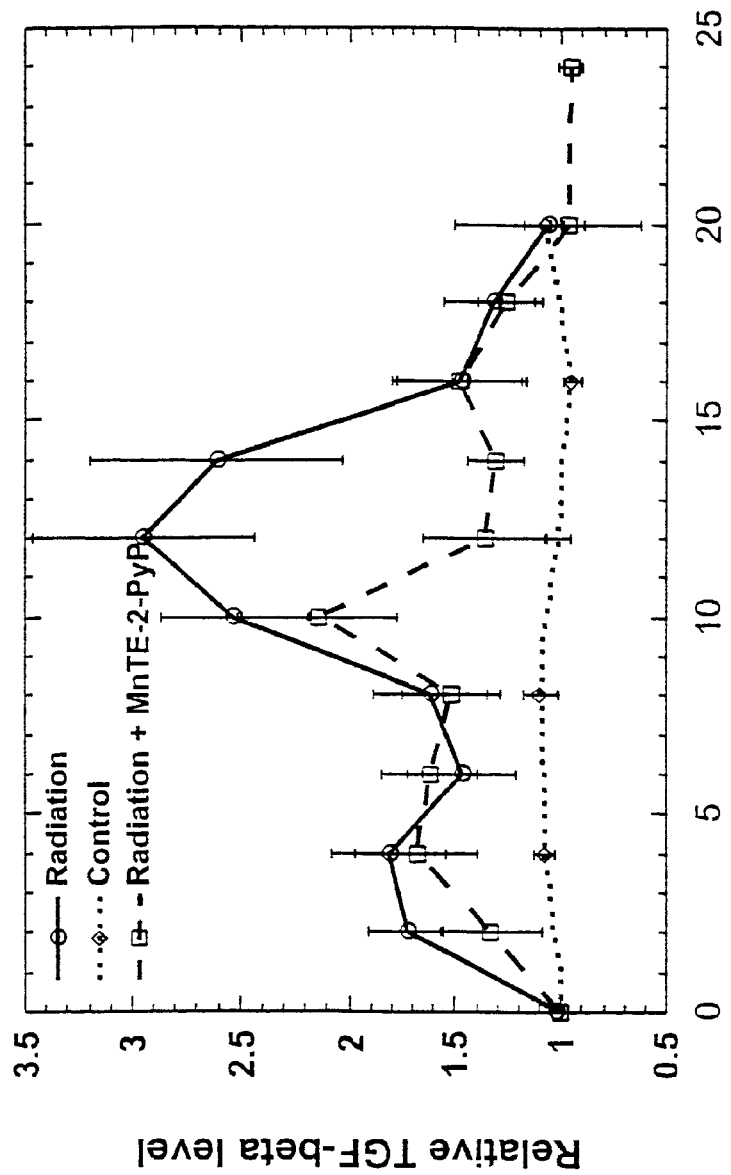

FIG. 14. Relative changes in plasma levels of TGF-β after 28 Gy of right hemothoracic irradiation.

Figure 15:
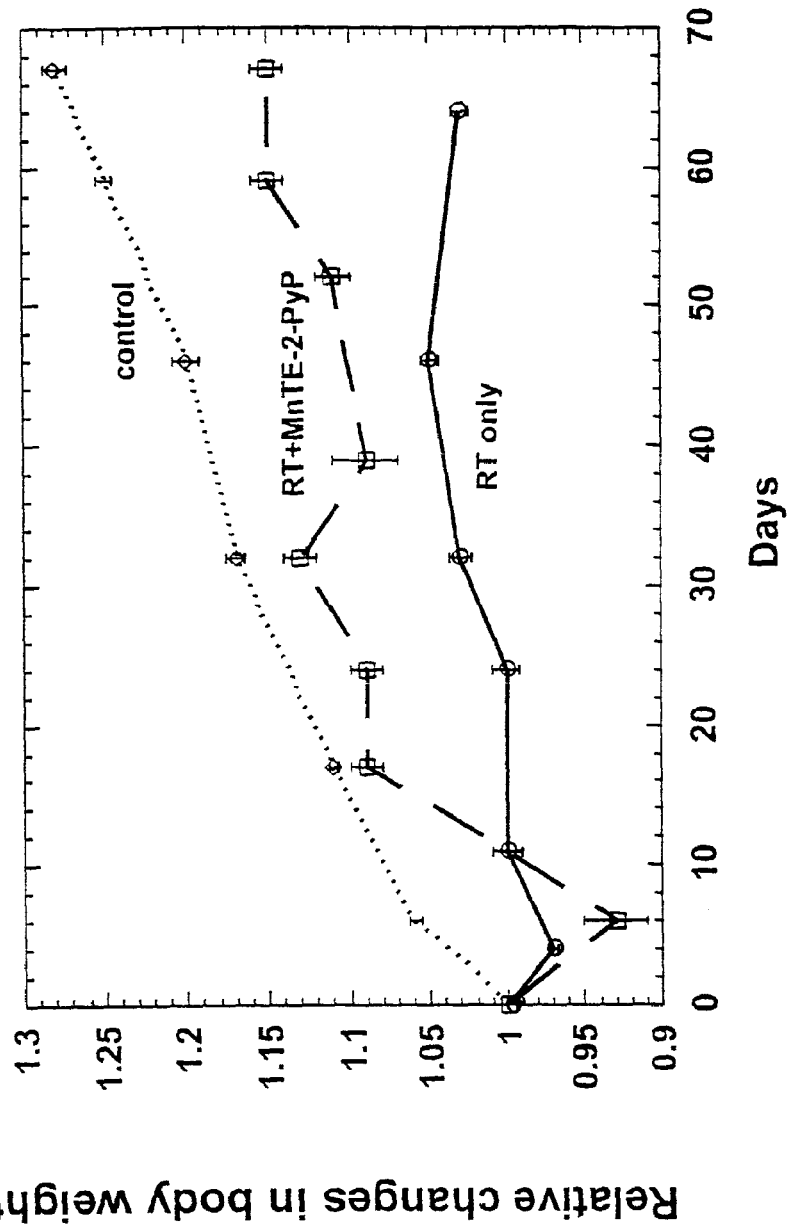

FIG. 15. Effects on body weight of radiation induced lung injury.

Figure 16:
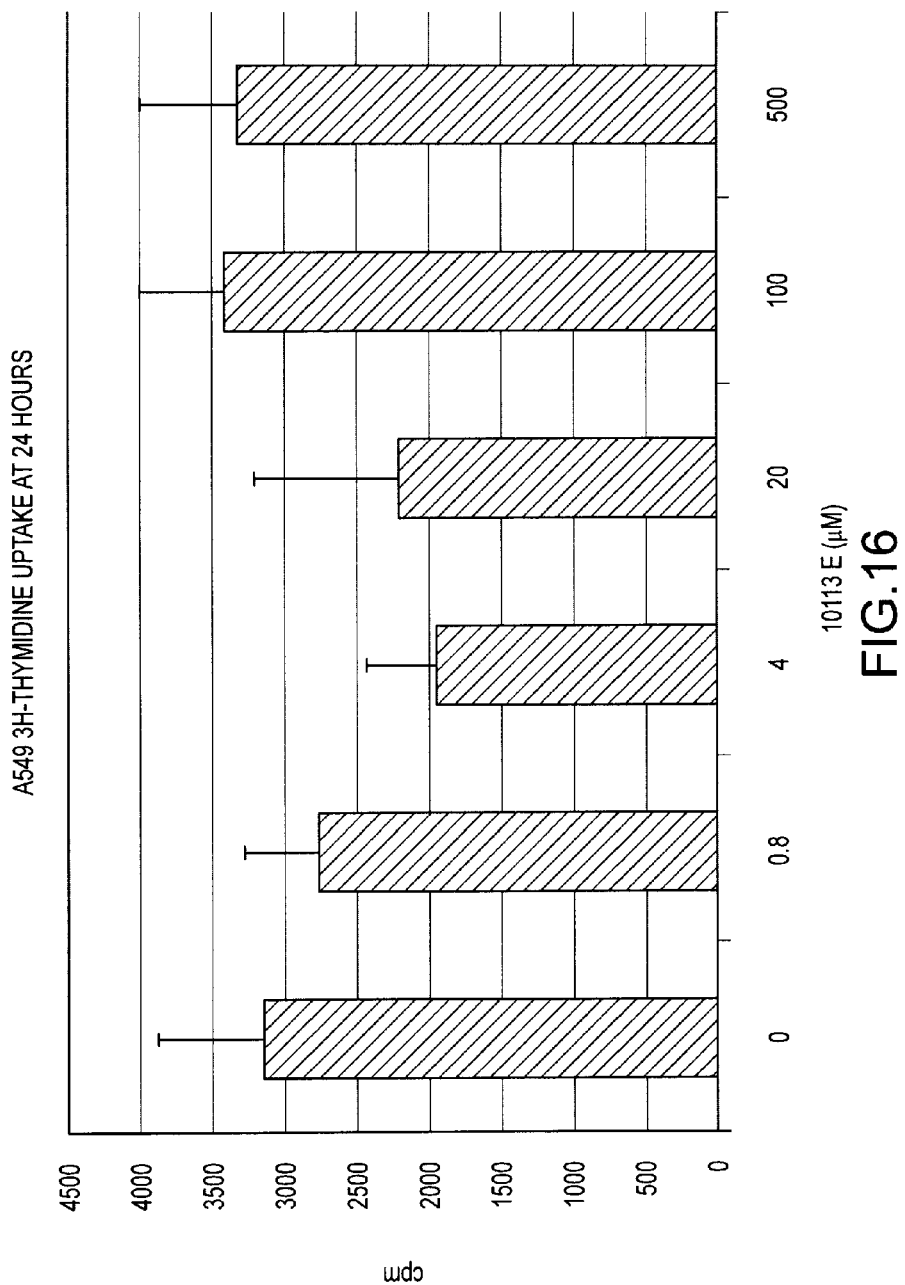

FIG. 16. A549 cells were grown 50% confluence in 24 well plates in complete media. Cells were then incubated for 24 hours with the above concentrations of drug and $^3$H-thymidine (to assess DNA synthesis). After three washes in PBS, the cells were homogenized and the radioactivity counted. At 4 µM MnTE-2-PyP, there was a 50% inhibition of incorporation of $^3$H-thymidine.

FIGS. 17A-17E. Effect of metalloporphyrins on human tumor cell (A549).

Figure 18:
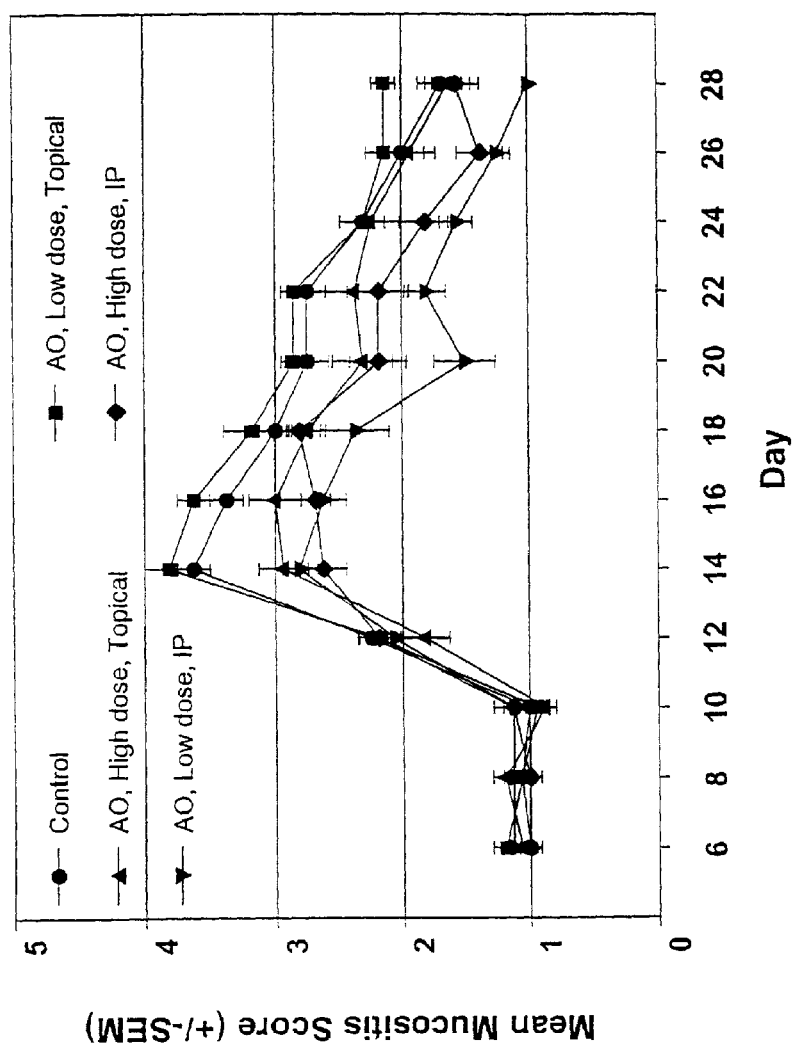

FIG. 18. Distribution of mucositis scores over time.

Figure 19:
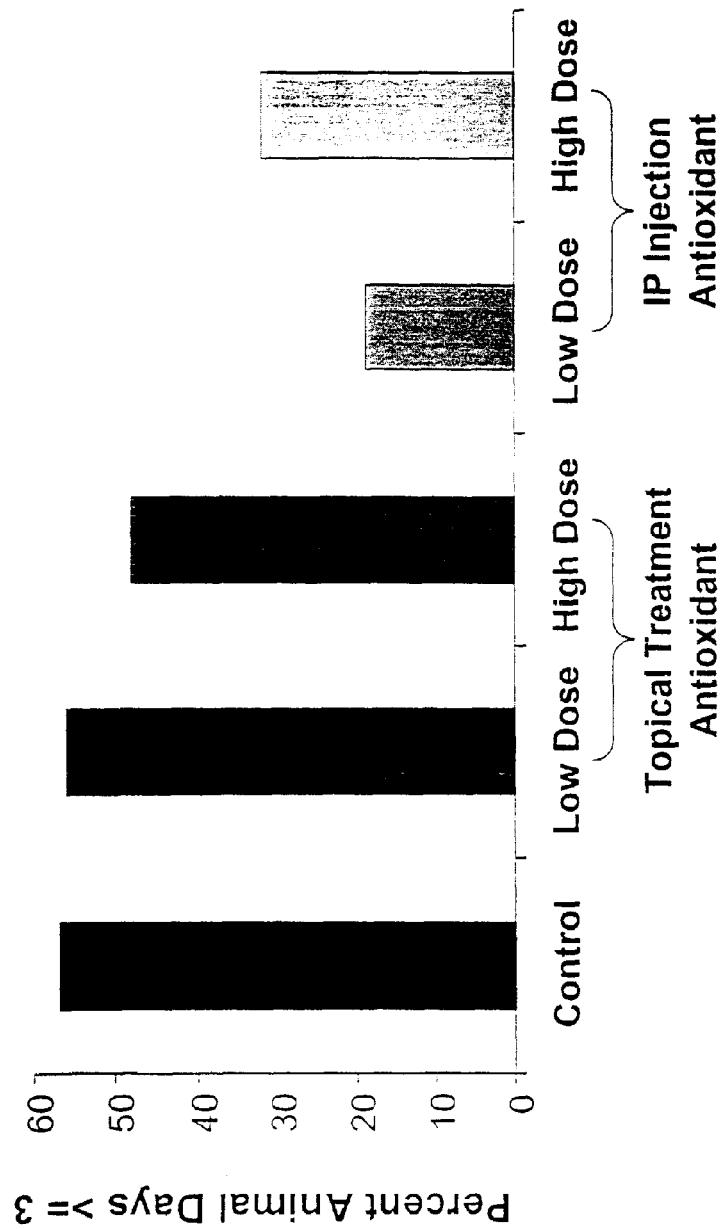

FIG. 19. Effect of SOD mimetic on the percent of days with mucositis scores ≥3.

DETAILED DESCRIPTION OF THE INVENTION

The present invention relates to methods of preventing or treating cancer using low molecular weight antioxidants (eg mimetics of scavengers of reactive oxygen species, including mimetics of SODs, catalases and peroxidases) as the active agent or as a chemo- and/or radio-protectant. The invention further relates to formulations suitable for use in such methods.

Mimetics of scavengers of reactive oxygen species appropriate for use in the present methods include methine (ie meso) substituted porphines and substituted tetrapyrroles, or pharmaceutically acceptable salts thereof (eg chloride or bromide salts). The invention includes both metal-free and metal-bound porphines and tetrapyrroles. In the case of metal-bound porphines and tetrapyrroles, manganic derivatives are preferred, however, metals other than manganese such as iron (II or III), copper (I or II), cobalt (II or III), or nickel (I or II), can also be used. It will be appreciated that the metal selected can have various valence states, for example, manganese II, III, IV or V can be used. Zinc (II) can also be used even though it does not undergo a valence change and therefore will not directly scavenge superoxide. The choice of the metal can affect selectivity of the oxygen species that is scavenged. Examples of such mimetics are shown in FIG. 1 and are described in U.S. Pat. No. 5,994,339, U.S. Pat. No. 6,127,356 and U.S. Pat. No. 6,103,714 and in U.S. application Ser. Nos. 09/184,982 and 09/880,124, 09/296,615, 09/490,537 and 09/880,075 (60/211,857) (these patents and applications are incorporated in their entirety by reference). Appropriate methods of synthesis are described in these patents and applications.

In addition to the mimetics described in the above-identified patents and applications, manganese salen compounds can also be used (Baudry et al, Biochem. Biophys. Res. Commun. 192:964 (1993)). Manganese macrocyclic complexes, such as those described by Riley et al (Inorg. Chem. 35:5213 (1996)), Deune et al (Plastic Reconstr. Surg. 98:712 (1996)), Lowe et al (Eur. J. Pharmacol. 304:81 (1996)) and Weiss et al (J. Biol. Chem. 271:26149 (1996)) can also be used. (See also U.S. Pat. Nos. 6,084,093, 5,874,421, 5,637,578, 5,610,293 and 6,087,493.)

Cancer types amenable to treatment in accordance with the invention include leukemias, myelomas, and solid tumors such as melanomas, lymphomas, sarcomas, and tumors of the lung, breast, prostate and colon.

In addition to being useful in cancer treatment, the compounds described herein can also be used as chemopreventatives, for example, in individuals diagnosed with preneoplastic conditions such as squamous metaplasia, cervical displasia, and polyposis of the colon. In addition, the present compounds can be administered to individuals predisposed to cancer or in remission in order to reduce the likelihood of tumor development.

The compounds of the invention can be used alone or in combination with other chemotherapeutic agents, such as bleomycin, cisplatin, adriamycin, and camptothicen. When used in combination therapy, the present compounds can increase the anti-tumor effect of chemotherapy as well as prevent toxicity, in whole or in part, resulting from free radicals produced by agents such as bleomycin, cisplatin and adriamycin. The present compounds can also be used in combination with radiation therapy and can both increase the efficacy of radiation therapy and serve to protect normal tissue from the effects of radiation treatment. The mimetics can further be used together with heat therapy, gene therapy, immunotherapy, or any combination of the above anti-tumor therapies, and improve the toxic/therapeutic ratio through increasing the anti-tumor effect and reducing toxicity to normal tissue by preventing damage (e.g., inflammation) resulting from free radical generation. A wide variety of normal tissues can be protected through the use of the present mimetics, including lung tissue, mucosa, gastrointestinal tract tissue, leucocytes, hair follicles, skin and bone marrow.

The compounds described above, metal bound and metal free forms, can be formulated into pharmaceutical compositions suitable for use in the present methods. Such compositions include the active agent (mimetic) to ether with a pharmaceutically acceptable carrier, excipient or diluent. The composition can be present in dosage unit form for example, tablets, capsules or suppositories. The composition can also be in the form of a sterile solution suitable for injection (e.g., subcutaneous, i.p. or i.v.) or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought. The compounds can also be encapsulated in lysosomes and thereby targeted to enhance delivery to tumors.

The dosage of the composition of the invention to be administered can be determined without undue experimentation and will be dependent upon various factors including the nature of the active agent (including whether metal bound or metal free), the route of administration, the patient, and the result sought to be achieved. A suitable dosage of mimetic to be administered IV or topically can be expected to be in the range of about 0.01 to 50 mg/kg/day, preferably, 0.1 to 10 mg/kg/day, more preferably 0.1 to 6 mg/kg/day. For aerosol administration, it is expected that doses will be in the range of 0.001 to 5.0 mg/kg/day, preferably, 0.01 to 1 mg/kg/day. Suitable doses will vary, for example, with the compound and with the result sought.

Certain aspects of the present invention will be described in greater detail in the non-limiting Examples that follows.

Example 1

Effect of SOD Mimetic on Tumor Growth and Response to Radiation Therapy

Acute pneuxnonitis and chronic fibrosis leading to impaired pulmonary function is the dose limiting toxicity of thoracic irradiation (TRT). This circumstance severely restricts the ability to deliver optimal doses of irradiation to patients with carcinoma of the lung (~160,000 new cases/ year). Standard radiotherapy for non-small cell lung cancer (NSCLC) typically consists of 66-70 Gy. Tumor control rates are very low with this dosage, however. The clinical problem is that local control is a sine qua non for disease cure. Higher doses have resulted in better local control rates, often with increased complications. Pulmonary toxicity from thoracic irradiation is also a significant problem in other settings including: combined modality treatment of Hodgkin's disease and esophageal cancer, chest wall irradiation after high dose chemo/ABMT (autologous bone marrow transplantation) in breast cancer, and bone marrow transplantation with total body irradiation.

Development of a method that will prevent and/or ameliorate radiation-induced normal tissue injury is needed. Among the many radioprotective agents that have so far been recognized, superoxide dismutase (SOD) is of particular interest. SOD has been shown to reduce the severity of radiation injury of lungs in rodents. However, clinical application of this naturally occurring enzyme is limited due to the short plasmatic half-life. The present study was undertaken to determine if an SOD mimetic would be more effective in preventing of reducing the extent of radiation induced normal tissue injury.

The effect of the MnTE-2-PyP (manganese(III) tetrakis(N-ethylpyridinium-2-yl)porphyrin) on tumor growth and radiation response in two tumor models has been tested. In mice with human melanoma tumors (B16) a significant inhibition of tumor growth was observed in animals receiving 6 mg/kg of SOD mimetic given i.p. Tumor doubling time in the control group of animals was 2 days whereas in animals receiving treatment, tumor-doubling time increased to 4 days. Therapeutic advantage from the modifier of radiation-induced normal tissue injury can only be achieved if the radioprotective agent does not also protect the tumor. The effect of the SOD mimetic. MnTE-2-PyP, on tumor growth and radiation response has been tested in a rat model. Impressive inhibition of tumor growth (>50%) was observed in the group of rats receiving the SOD mimetic. After radiation treatment (21 Gy) a significant tumor response was observed suggesting that the SOD mimetic agent does not protect tumor from irradiation. It appears that the rats receiving the mimetic had a significant inhibition of the post-radiation tumor regrowth.

The results are shown in FIGS. 2A and 2B.

A similar experiment (FIG. 2C) demonstrated that AEL 10113 treatment limited tumor growth and did not diminish the effect of radiation on tumor growth.

Example 2

Effect of SOD Mimetics on Tumor Growth and Angiogenesis

Experimental Details
Animals

The experiments were performed with female Fisher-344 rats. All animals were housed 4 per cage and maintained under identical standard laboratory conditions during which food and water were provided ad libitum. Rats weighing 150-170 g were anaesthetized prior to tumor or chamber transplantation by an intraperitoneal injection of ketamine (67.5 mg/kg) and xylazine (4.5 mg/kg).

Tumor

R3220 AC mammary adenocarcinoma was transplanted on the right hind leg. When the tumors reached 0.8-1 cm in diameter, the rats were randomized into 4 groups to receive 1) Saline (control); 2) Drug 10150; 3) Drug 10113; 4) Drug 10201. Drugs were given daily in dose of 6 mg/g i.p. The tumor size was measured twice a week. (FIG. 3).

Z-Chambers:

These chambers are constructed from customized plexiglass rings with internal diameter of 10 mm and have a pore on the side. The two open surfaces are covered by nylon mesh (pore size 180 microns, Millipore, Mass.) and glued to the rings. Fibrinogen (Human fibrinogen, plasminogen depleted, CalBiochem) is prepared in DMEM, Gibco BRL) and a concentration of 4-5 mg/ml is utilized for the studies. Although the Fischer rats used in the study are immune competent, this purified batch of fibrinogen has been recognized to be very well conserved across species lines. It has already been shown that early angiogenic response to human fibrinogen is very similar to rat fibrinogen in fibrin gel chambers. The two different types of fibrinogen have also been tested in the Z-Chambers and no difference was found in angiogenic and healing response. Human fibrinogen was used.

The Fibrin Z-Chambers have fibrinogen solution poured inside the chamber through the pore and followed by 2 units of thrombin. For tumor Z-Chambers, first R3230 Ac rat mammary carcinoma cells grown in tissue culture were harvested by standard procedures and the resultant pellet was washed three times with DMEM. Fibrinogen solution was added to the pellet to make the final concentration of cells approximately 2.5 million cells/ml. This tumor cell/fibrinogen solution was added to the chambers through the pore and again followed by 2 units of thrombin. After addition of thrombin, fibrin was allowed to gel inside the chambers for 15 minutes before implantation in animals. Fischer 44 rats were anesthetized, hair was removed using clippers and the surface was surgically prepared. Two small incisions were made in the dorsum along the midline about 4 cm apart. Fascia was blunt dissected and small pockets were created on both sides along the midline incisions. Four Z-chambers were successfully implanted in those pockets per animal. There is little difference in response (amount of granulation or tumor tissue generated) between the 4 chambers/animal and among the chambers/animals in one group. Also, no difference in response has been observed whether 1 or 4 chambers (Fibrin or Tumor Z-chambers) are implanted per animal in initial studies with this model system.

The Z-Chambers were harvested on day 1 or 12 post surgery. The tissues were cut out from the chamber and were preserved in 10% formalin for paraffin embedding. For evaluation of the Z-Chambers, pictures of the sections of each sample stained with hematoxylin and eosin were taken at 10×. Pictures were taken at the maximum depth of tissue observed in the section. The depth of either the tumor tissue (tumor growth) or granulation tissue (wound healing) was measured with calipers on the 4×6 inch print. In this way of measurement, bias has purposefully been given to the treated tissue since in many treated samples the tissue never homogenously filled the chamber at that depth. All measurements were done in a blinded fashion. (FIG. 4)

Immunohistochemistry:

Immunohistochemistry was carried out using procedures described by Hsu et al (Hsu et al., j. Histochem. Cytochem. 29:577-580 (1981)). Briefly, paraffin embedded tissues were sectioned (5 microns) and antigen retrieval was performed using citrate buffer from Biogenex (San Ramon, Calif.). Tissues were treated with primary antibody against tissue transglutaminase (TG100, 1:10, endothelial cell marker, non-reactive to Factor XIIIa) (Neomarkers, Calif.) for 1 hour at 37° C. Secondary antibody (Jackson ImmunoResearch. PA) and tertiary. (Vector, Calif.) antibodies were incubated for 25 minutes at 37° C. and the location of the reaction was visualized with 3,3-diaminobenzidine tetrahydrochloride Sigma (St. Louis, Mo.). Slides were counterstained with hematoxylin and mounted with coverslips. Controls for the immunohistochemistry were treated with mouse IgG instead of primary antibody and were negative in any reactivity. Hematoxylin & Eosin and Masson's trichrome (MT) was carried out as described by Sheehan (Sheehan et al, In: Theory and Practice of Histotechnology, Battelle Press, Columbus, Ohio (1980)) to evaluate collagen (green color) on the fibrin Z-chamber sections. Microvessel density was calculated as described by Weidner et al (Weidner et al, J. New Engl. J. Med. 324:1-8 (1991)). Briefly, six hot spots or areas with highest vessels marked by the vessel marker at a high power field (400×) per sample section were selected and number of blood vessel counted. The data was then pooled for the control and treated tissues to arrive at the mean values for each group. All measurements were done by two independent pathologists in a blinded fashion. (FIG. 5)

Example 3

Attenuation of Bleomycin-Induced Pulmonary Fibrosis

Experimental Details

Preparation of manganese (III) tetrakis-(4-benzoic acid) porphyrin (MnTBAP). A 1.5 M excess of manganese chloride (Fisher, Fair Lawn, N.J.) was incubated with tetrakis-(4-benzoic acid) porphyrin ($H_2$TBAP, Aldrich, Milwaukee, Wis.) that was dissolved in water and the pH titrated to 7.0 with 0.1 N sodium hydroxide. The reaction mixture was stirred and heated to 80° C. The pH of the reaction was monitored every hour and readjusted to 7.0 with 0.1 N sodium hydroxide. Metal ligation was followed spectrophotometrically (UV-2101 PC, Shimadzu, Columbia, Md.). Over time, the Soret band for the $H_2$TBAP ($\lambda$=415 nm) disappeared with the emergence of the Soret band for MnTBAP ($\lambda$=468 nm) that has an extinction coefficient of $\epsilon$=9.3×10$^4$ M$^{-1}$ cm$^{-1}$ (Harriman et al, J. Chem. Soc. Faraday Trans. 275:1532-42 (1979)). Excess metal was removed by batch adsorption with chelex-100 resin (BioRad, Hercules, Calif.). The product was passed through a 0.22µ filter (Millipore, Bedford, Mass.) and stored in the dark at 4° C. until used. The purity of the MnTBAP was found to be greater than 90% by HPLC analysis.

Animals and treatments. Balb/c male mice that were 6-8 weeks of age were utilized in these studies (Taconic, Germantown, N.Y.). Mice were acclimated to 22° C. in an environmentally controlled room (12-hr light cycles) at least 6 days prior to treatment. Toxicity studies were employed using a moving average method previously described by Weil (Weil, Biometrics 8:249-263 (1952)). Groups of 4 mice were given MnTBAP (50, 88, 153 and 268 mg/kg, ip) and observed over a 48 hour time period. Mice were given one bolus dose of MnTBAP (10 mg/kg, ip) dissolved in phosphate buffered saline (PBS) and blood and lung tissue levels of MnTBAP were determined at several different time points for pharmacokinetic analysis. Separate sets of mice were used for the lung fibrosis study. Mice were randomized into two groups of 10 mice that received intratracheal bleomycin (3.5 U/kg, ICN, Aurora, Ohio) or an equivalent volume of saline (50 µl). Half the animals in these groups also received MnTBAP (5 mg/kg, ip) or an equivalent volume of PBS (1 ml/kg, ip) twice daily for 14 days.

Analysis of MnTBAP in serum and lung homogenates. Mice were anesthetized with pentobarbital (60 mg/kg, ip) and blood was obtained by a cardiac puncture. Blood samples were placed in 1.5 ml tubes and left at room temperature to clot for 30 minutes. Serum was removed after spinning the blood samples at 1000×g for 10 minutes. Serum samples were stored at −20° C. until used. Lungs were perfused with phosphate buffered saline through the pulmonary artery to clear blood from the vasculature. The lungs were removed and homogenized in 10 mM tris-HCl buffer containing 1.15% potassium chloride at pH 7.5 with a polytron (Turrax-25, Janke & Kunkel, Germany). Lung homogenates were stored at −20° C. until used. MnTBAP was extracted from serum (50 µl) and lung homogenates (100 µl) with 800 µl of methanol, vortexed for 2 minutes and centrifuged at 7,000×g. The top layer was removed and the extraction process was repeated twice. The pooled fractions were evaporated to dryness and re-dissolved in 100 µl of water. This was then transferred to HPLC vials for analysis. Standards were prepared in control lung or serum samples and extracted as described above. MnTBAP was quantitated using a HPLC (Ranin, Emeryville, Calif.) equipped with a UV-1 detector set at $\lambda=468$ nm and a flow rate of 1 m/min. The stationary phase consisted of a YMC ODS C-18 column (1.4×100 mm) and a mobile phase consisting of 60% solution A and 40% solution B (solution A: water+0.1% trifluoroacetate, solution B: acetonitrile/water (90:10)+0.1% trifluoroacetate). MnTBAP extracted from lung homogenates and serum eluted at 5.9 minutes. Recovery of MnTBAP from samples using the extraction method described above ranged from 85-91%. The linear regression analysis of the standard curves were $r^2>0.99$.

Pharmacokinetics. A standard two-compartment model was used to calculate serum and tissue half-life (Shargel et al, Applied Biopharmaceutics and Pharmacokinetics. New York: Appleton-Century-Crofts (1980)). The data was fitted to the following equation: $C_d=Ae^{-at}+Be^{-bt}$; where (a) and (b) are rate constant for the distribution phase and elimination phase, respectively. The constants (A) and (B) are intercepts on the y-axis for each exponential segment of the curve. The constant (B) was used as an estimate of the peak serum and lung MnTBAP levels, respectively. The calculated values were computer generated from Prizm 3.0 (GraphPad, San Diego, Calif.).

Noninvasive measurement of airway constriction in mice. The baseline resistance in unrestrained, conscious mice was assessed by whole body barometric plethysmography (Buxco Electronics, Troy, N.Y.). The techniques used were similar to those described by Zhu et al, J. Clin. Invest. 103(6):779-88 (1999)). Mice were placed in whole body plethysmographs with fast differential transducers interfaced to a computer. Measurements were made of respiratory rates, tidal volumes and enhanced pause ($P_{ENH}$). Airway constriction was expressed as $P_{ENH}=[(T_e/0.3T_r)-1]\times[2P_{ef}/3P_{if}]$, where $T_e$=expiratory time (seconds), $T_r$=relaxation time (seconds), $P_{ef}$=peak expiratory flow (ml), and $P_{if}$=peak inspiratory flow (ml/second). Animals were allowed to equilibrate in the chambers for 15 minutes and then $P_{ENH}$ was calculated over a 5-minute period.

Hydroxyproline measurement. The lungs were dried at 80° C. until a constant weight is obtained. The dried lungs were hydrolyzed under vacuum in a glass vial in 1 ml of 12 N HCl at 120° C. overnight. The samples were lyophilized and assayed for hydroxyproline content using chloramine-T as previously described (Woessner, Arch. Biochem. Biophys. 93:440-447 (1961)).

Histopathology. The lungs were fixed in 4% paraformaldehyde for 24 hours and then processed for paraffin embedding. Sections of lung were stained with routine hematoxylin and eosin or with a Masson trichrome stain to assess the degree of fibrosis. The extent of lung injury and fibrosis was graded by four pathologists, blinded as to the treatment group, on a scale of one (no injury) to ten (severe injury/fibrosis). The major criteria examined included interstitial thickening, collagen deposition, type 2 cell hyperplasia, and inflammatory cell infiltration.

Statistical Analyses. Data was analyzed using a two-way analysis of variance (ANOVA) or a one-way ANOVA if no significant interactions were found with the two-way ANOVA. Significant differences between groups were assessed using a Newman-Keuls multiple comparison test. Data was analyzed using a computer program, Prizm (Graph Pad Software, San Diego, Calif.). Statistical significance was set at $p<0.05$.

Results

Toxicity and Pharmacokinetic Assessment of MnTBAP in Mice

To test the efficacy of the catalytic antioxidant MnTBAP (FIG. 6) in a model of pulmonary fibrosis, it was necessary to establish a rationale dosing regiment that would result in MnTBAP lung levels without drug toxicity. MnTBAP toxicity was assessed using a moving average method that consisted of four geometric dose groups (50, 88, 153 and 268 mg/kg, ip) of 4 mice each over 48 hours. There were no deaths associated with the 50 mg/kg group and 1 death in the 88 mg/kg group. The two highest doses were lethal to the mice. MnTBAP had a calculated $LD_{50}$ of 100 mg/kg with a 95% confidence interval of 98-104 mg/kg. A 10 mg/kg ip dose of MnTBAP was then chosen to conduct pharmacokinetic studies based on the toxicity data. Serum and lung tissue levels of MnTBAP were determined at 0.3, 0.5, 1, 2, 4, 6 and 24 hours after drug treatment. The data was fitted to a two compartment pharmacokinetic model and the distribution and elimination half-lives were calculated from the data fitted curves (FIG. 7). MnTBAP rapidly equilibrated into the lung from the bolus ip injection with a distribution half-life of 14 minutes (Table 2). The estimated peak serum and lung tissue concentration of MnTBAP was 42 mg/L and 80 µg/g protein, respectively. The elimination half-lives of MnTBAP from the serum and lung were identical at 9.5 hours. These data indicate that: 1) MnTBAP does not accumulate in the lung; and 2) a twice a day dosing regimen based on its half-life of 9.5 hours.

TABLE 2

Pharmacokinetic profile of MnTBAP (10 mg/kg, ip) in mice.

| | Peak Level ($C_o$) | Distribution half-life ($T_{1/2}$) | Elimination half-life ($T_{1/2}$) |
|---|---|---|---|
| Serum | 42 mg/L | 27 min | 9.5 hrs |
| Lung | 80 µg/g protein | 14 min | 9.5 hrs |

Attenuation of Bleomycin-Induced Lung Fibrosis by MnTBAP

Mice were randomized into 4 groups using a two by two contingency table where two groups received either saline or bleomycin (3.5 U/kg body weight) by intratracheal instillation. Two groups also received either saline or MnTBAP (5 mg/kg body weight) by ip injection twice daily for 14 days. The groups that received bleomycin lost significantly more weight than vehicle controls over 14 days with a maximum average loss of 20% of their initial body weight (FIG. 8). MnTBAP treatment did not cause weight loss as compared to the saline control group. The group of mice that received both bleomycin and MnTBAP had less weight loss than the bleomycin group from day 5 to 14 with a maximum average loss of 10%.

Bleomycin given by intratracheal instillation produces a marked airway and alveolar fibrotic response (Evans et al, Am Rev. Respir. Dis. 125(1):89-94 (1982)). Mice were assessed for changes in airway function by measuring a marker, enhanced pause ($P_{ENH}$), of airway narrowing using non-invasive whole body barometric plethysmography. Intratracheal bleomycin treatment produced a 3-fold increase in the $P_{ENH}$ index of airway constriction after 14 days (FIG. 9A). MnTBAP treatment alone did not affect the $P_{ENH}$ marker, but caused a 30% decrease in airway constriction produced by bleomycin treatment. Lung fibrosis was also assessed by measuring hydroxyproline content in the lung as an index of collagen accumulation. Bleomycin treatment produced a 2-fold increase in hydroxyproline content of the lung after 14 days (FIG. 9B). MnTBAP treatment had little effect on hydroxyproline content of the lung, but produced a 23% decrease in hydroxyproline content caused by bleomycin treatment. Increases in both $P_{ENH}$ and hydroxyproline content correlated well with fibrotic changes seen by histopathology assessment.

One lung from each mouse was instillation fixed with 4% paraformaldehyde and paraffin embedded for histopathology assessment. Tissue sections were stained with hematoxylin and eosin or with Masson trichrome stain to assess the degree of lung injury/fibrosis. Bleomycin treatment produced an inflammatory response characterized by substantial thickening and loss of normal alveolar structure, type 2 cell hyperplasia, and an intense acute inflammatory response in alveolar spaces and interstitial spaces (FIG. 10A) as compared to control lungs (FIG. 10C). Lung sections stained for collagen with a trichrome stain showed marked increased collagen accumulation predominately in the thickened alveolar regions and to a lesser extent around small bronchioles (FIG. 10G) compared to control lungs (FIG. 10E). MnTBAP treatment alone had no effect on lung histology (FIGS. 10B and 10F), but attenuated the marked interstitial thickening and inflammatory responses produced by bleomycin (FIG. 10D). MnTBAP treatment also decreased the collagen accumulation as assessed by trichrome staining (FIG. 10H). Lung sections were semi-quantitatively assessed for fibrotic response on a scale of 0-8 with a score of one representing a normal lung and a score of 8 representing a very severe fibrotic lung. Lung sections were randomized and scored blinded. Bleomycin treatment produced a 2-fold increase in the pathology score as compared to the control group (FIG. 11). MnTBAP treatment had no effect on the pathology score, but attenuated the bleomycin pathology score by 28%. These results closely support the physiologic and biochemical indices where bleomycin produced about a 2-fold increase in the various indices and MnTBAP attenuated these increases by roughly 30%.

Example 4

Protection of Radiation-Induced Lung Injury Using SOD Mimetic and Assessment of Post Radiation Lung Fibrosis AEOL 10113 was tested (6 mg/kg/day for 5 days beginning on the day of irradiation) in a rat model of radiation-induced lung injury as assessed by breathing rate (animals with lung injury have a more rapid respiration rate), and chemical and microscopic measures of fibrosis. During the follow-up period of 6 months, 4 of the 9 rats receiving radiation only developed severe respiratory distress and were euthanized. In the group of rats treated with radiation plus AEOL 10113, only 1 of the 9 rats developed respiratory distress and was euthanized. Breathing rate data were analyzed on a last observation carried forward (LOCF) data set, in which the last observation for rats euthanized due to respiratory distress was imputed to subsequent weeks. There was a significant (log ranks p=0.0011) delay (approximately 3.4 weeks) in the development of radiation-induced lung injury (assessed by an increase in breathing rate) in animals treated with AEOL 10113 (FIG. 12). Furthermore, the magnitude of the increase in breathing rate was reduced by an average of 34% at endpoint indicating the ability of AEOL 10113 to significantly reduce the severity of functional deficit associated with radiation-induced lung injury.

Six months after radiation all remaining animals were euthanized. At that time, the right upper lung lobe was removed and processed to quantify the extent of lung fibrosis based on hydroxyproline content. FIG. 13A shows there were no differences in the hydroxyproline content of the right upper lobe between the control group (no radiation, no AEOL 10113) of animals and those that received AEOL 10113 without radiation. However, a significant increase in hydroxyproline content per gram of dry or wet lung was observed in animals receiving radiation only (28 Gy single dose). Thus, administration of AEOL 10113 before and for 4 days after radiation resulted in a significant reduction (p<0.05) in hydroxyproline content in both wet and dry upper right lobe.

Radiation-induced lung fibrosis was also assessed using histopathology (FIG. 13B). Lungs were fixed in 10% neutral buffered formalin. Five-micron thick sections were stained with hematoxylin and eosin or Masson trichrome and examined microscopically. Slides were systematically scanned in a microscope using a ×10 objective. Each successive field was individually assessed for severity of interstitial fibrosis and allotted a score of between 0 and 8. These data indicate AEOL 10113 also reduced radiation-induced lung fibrosis.

Example 5

Changes in Plasma Levels of TGF-β as an Indicator of RT-Induced Lung Injury

Of particular interest is whether measurements of TGF-β in the plasma during treatment might reflect radiation-induced local changes in TGF-β expression and whether modification of pulmonary toxicity will be reflected in plasma levels of TGF-β. Previously, extensive studies have been conducted to determine the relationship between plasma TGF-β levels and development of RT-induced pulmonary injury. In rats, significant changes in plasma TGF-β levels were found to occur 20 weeks after 18 Gy hermithoracic irradiation. An increase in plasma TGF-β levels coincided with an increase in breathing frequency which was most pronounced between 22 and 28 weeks after irradiation. Immunohistochemistry results indicated an increase in TGF-β staining at 4 weeks after irradiation with continuous overexpression during both the inflammatory and fibrotic phases. These data indicate that, in rats, plasma TGF-β level is a potential marker of normal tissue injury after hemithoracic irradiation. (See FIG. 14.)

Example 6

Effects of Body Weight of Radiation-Induced Lung Injury

Studies were performed to evaluate changes in body weight after irradiation and to assess the radioprotective effect of MnTE-2-PyP on radiation-induced pulmonary injury in rats. The body weight and lung function of the animals were measured every two weeks after irradiation in three groups of animals: control, radiation alone and radiation+MnTE-2-PyP. A single dose of 28 Gy was delivered to right hemithorax and 6 mg/kg of MnTE-2-PyP was given daily i.p. for 5 days after irradiation. Unrestrained rats were placed in a 1500 ml whole body plethysmograph tube connected to a pressure transducer for a breathing rate measurements. Changes in the air pressure were recorded and displayed on a calibrated chart recorder. The mean of five measurements was performed on each animal. During the first week after irradiation, a significant decrease in body weight was observed in both groups of animals receiving hemithoracic radiation. However, animals receiving MnTE-2-PyP in addition to radiation had significantly better recovery of the body weight loss after hemithoacic irradiation than animals receiving radiation only. The results are shown in FIG. 15.

Example 7

Manganic Porphyrins Differentially Inhibit Tumor Cell Proliferation

Two non-tumor cell lines (rat lung epithelial cells, L2; bovine endothelial cells, CPA-47) and one tumor cell line (human adenocarcinoma lung cells, A549) were examined for cell proliferation in the presence or absence of manganic porphyrins (see FIG. 16). Cells were plated in 24 well plates at 10,000 cells per well in the presence or absence of 100 μM MnTBAP, MnTM-4-PyP and their zinc analogs for 48 hours. None of the compounds produced cytotoxicity (as measured by LDH release) at this concentration. Manganic porphyrins selectively inhibited tumor cell proliferation up to 50% compared to tumor cell growth without manganic porphyrins. In contrast, manganic porphyrins had no suppressive effects on non-tumor cell growth. This finding supports the in vivo tumor transplantation studies in that manganic porphyrins can selectively inhibit tumor cell proliferation and may be efficient chemotherapeutic agents.

Example 8

Manganic Porphyrins Selectively Potentiate the Cytotoxic Effects of Redox Cycling Cytotoxic Agents in Tumor Cells Two non-tumor cell lines (rat lung epithelial cells, L2; bovine endothelial cells, CPA-47) and one tumor cell line (human adenocarcinoma lung cells, A549) were examined for cell proliferation in the presence or absence of manganic porphyrins. Cells were plated in 24 well plates at 10,000 cells per well in the presence of cytotoxic agent (0-10 mM paraquat) for 24-48 hours plus increasing concentrations of MnTBAP, MnMm-4-PyP and their zinc analogs. Both MnTBAP and MnTM-4-PyP potentiated paraquat-mediated cytotoxicity in the tumor cells (A549) with MnTBAP being more efficient than MnTM-4-PyP. In contrast, both manganic porphyrins protected non-tumor cells against the cytotoxic effects of paraquat. These finding suggest that the manganic porphyrins may provide selective potentiation of the other redox cycling cytotoxic chemotherapeutic such as bleomycin and adriamycin in tumor cells while protecting non-tumor cells against the damaging effects of these cytotoxic agents (see FIG. 17).

Example 9

The Effect of an SOD Mimetic on the Incidence and Course of Oral Mucositis Induced by Acute Radiation in Hamsters Oral ulcerative mucositis is a common, painful, dose-limiting toxicity of drug and radiation therapy for cancer. The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of patients receiving antineoplastic drug therapy. The frequency and severity are significantly greater among patients who are treated with induction therapy for leukemia or with many of the conditioning regimens for bone marrow transplant. Among these individuals, moderate to severe mucositis is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through three stages:

Inflammation accompanied by painful mucosal erythema, which can respond to local anesthetics.

Painful ulceration with pseudomembrane formation and, in the case of myelosuppressive treatment, potentially life-threatening sepsis, requiring antimicrobial therapy. Pain is often of such intensity as to require parenteral narcotic analgesia.

Spontaneous healing, occurring about 2-3 weeks after cessation of anti-neoplastic therapy.

Standard therapy for mucositis is predominantly palliative, including application of topical analgesics such as lidocaine and/or systemic administration of narcotics and antibiotics. Currently, there is no approved treatment for mucositis.

The complexity of mucositis as a biological process has only been recently appreciated. It has been suggested that the condition represents a sequential interaction of oral mucosal cells and tissues, pro-inflammatory cytokines and local factors such as saliva and the oral microbiota. While epithelial degeneration and breakdown ultimately result in mucosal ulceration, it appears that the early changes associated with radiation-induced mucosal toxicity occur within the endothelium and connective tissue of the submucosa. Electron microscopic evaluation of mucosa within 1 week of radiation shows damage to both endothelium and connective tissue, but not epithelium. Such injury is likely mediated by free radical formation. It appears that the overall mechanism for mucositis development is similar for both radiation and chemotherapy. (Eldor et al. Semin. Thromb. Hemost. 15:215-225 (1989)).

The involvement of reactive species in the initiation of oral mucositis makes it reasonable to hypothesize that antioxidants may be effective in preventing or alleviating symptoms of this adverse consequence of cancer therapy. In fact, some literature exists suggesting that antioxidants may be effectively used in treating oral mucositis. Consistent with these findings are numerous studies showing attenuation of radiation-induced skin damage or oxidant-mediated carcinogenesis by certain antioxidants. (Plevova, Oral Oncol 35; 453-470 (1999)).

As such, studies investigating the use of antioxidants in oral mucositis are warranted, particularly in light of the absence of consistently effective standard treatments. However, to date antioxidants tested have non-specific scavengers of reactive species. No catalytic antioxidants have been examined or proposed to effect the course of cancer-therapy induced mucosistis.

The objective of the study described below was to evaluate the effect of two doses of a proprietary catalytic antioxidant, administered topically and by injection, on the frequency, severity and duration of oral mucositis induced by acute radiation.

Experimental Details

Forty hamsters were given an acute radiation dose directed to their oral mucosa. Test materials will be applied by injection, or topically (three times per day) beginning the day before radiation and continuing until day 20. Mucositis were evaluated on alternate days beginning on day 6 (day of radiation=day 0) and continuing until the conclusion of the experiment on day 28.

Forty (40) hamsters were used. The hamsters were randomized into five (5) groups of eight (8) animals each. Each group was assigned a different treatment of 0.2 ml tid as follows:

| Group 1 | Water or PBS Control | day-1 to day 20. |
| Group 2 | 10150, 0.25 mg/ml, tid, topical (1.5 mg/kg/day) | day-1 to day 20. |
| Group 3 | 10150, 1 mg/ml, tid, topical (6 mg/kg/day) | day-1 to day 20. |
| Group 4 | 10150, 0.25 mg/ml, tid, ip (1.5 mg/kg/day) | day-1 to day 20. |
| Group 5 | 10150, 1 mg/ml, tid, ip (6 mg/kg/day) | day-1 to day 20 |

Mucositis Scoring

Parameters measured included the mucositis score, weight change and survival. For the evaluation of mucositis, the animals were anesthetized with inhalation anesthetics (Phenobarbital or Halothane), and the left pouch everted. Mucositis was scored both clinically during the laboratory portion of the study and in a blinded manner (at the conclusion of the study). Clinical scoring was performed by visual comparison to a validated photographic scale, ranging from 0 for normal, to 5 for severe ulceration.

In descriptive terms, this scale is defined as follows:
Score: Description:
0 Pouch completely healthy. No erythema or vasodilation
1 Light to severe erythema and vasodilation. No erosion of mucosa
2 Severe erythema and vasodilation. Erosion of superficial aspects of mucosa leaving denuded areas. Decreased stippling of mucosa.
3 Formation of off-white ulcers in one or more places. Ulcers may have a yellow/gray due to pseudomembrane. Cumulative size of ulcers should equal about ¼ of the pouch. Severe erythema and vasodilation.
4 Cumulative seize of ulcers should equal about ½ of the pouch. Loss of pliability. Severe erythema and vasodilation.
5 Virtually all of pouch is ulcerated. Loss of pliability (pouch can only partially be extracted from mouth)

A score of 1-2 is considered to represent a mild stage of the disease, whereas a score 3-5 is considered to indicate moderate to severe mucositis.

Results 10150 administered IP (0.2 ml of 0.25 mg/ml solution TID, 1.5 mg/kg/day) significantly reduced the incidence of severe mucositis as evidenced by a 59% reduction in the percent of days with Mucositis Scores ≥3 as shown in Table 3. A similar decrease was observed in the higher dose IP group, but not in either group treated by topical dosing at these concentrations.

TABLE 3

| Group | Days >= 3 | Days < 3 | Total Days | % Days >= 3 | Chi Sq v Control | P Value |
|---|---|---|---|---|---|---|
| Control | 88 | 104 | 192 | 45.8 | — | — |
| AO low dose topical | 83 | 99 | 182 | 45.6 | 0.004 | 0.953 |
| AO high dose topical | 73 | 119 | 192 | 38.0 | 2.096 | 0.148 |
| AO low dose IP | 36 | 156 | 192 | 18.8 | 30.980 | <0.001 |
| AO high dose IP | 60 | 132 | 192 | 31.3 | 8.015 | 0.005 |

Chi-square analysis of the total number of days the animals in each group spent with a score of three or more. This statistic is a measure of severity of ulceration, a clinically important outcome. Significant efficacy is indicated in red.

Repeated studies gave the results set forth in Table 4.

TABLE 4

Summary of mucositis findings with 10150

| Study | Dose | N | Route | Percent Days > 3 | P-value |
|---|---|---|---|---|---|
| INC-01 | Control | 8 | | 45.8 | |
| | 0.25 mg/ml | 8 | IP | 18.8 | 0.001 |
| | 1 mg/ml | 8 | IP | 31.3 | 0.005 |
| | 0.25 mg/ml | 8 | Topical | 45.6 | 0.953 |
| | 1 mg/ml | 8 | Topical | 38 | 0.148 |
| INC-02 | Control | 8 | | 43.3 | |
| | 0.25 mg/ml | 8 | IP | 28.6 | 0.004 |
| | 1.5 mg/ml | 8 | IP | 27.6 | 0.002 |
| | 1.5 mg/ml | 8 | Topical | 37.5 | 0.298 |
| | 5 mg/ml | 8 | Topical | 27.6 | 0.002 |
| INC-03 | Control | 7 | | 33.3 | |
| | 1 mg/ml | 7 | IP | 38.1 | 0.113 |
| INC-04 | Control | 7 | | 43.9 | |
| | 0.25 mg/ml | 7 | IP | 47.3 | 0.485 |
| INC-05 | Control | 8 | | 68.8 | |
| | 0.25 mg/ml | 8 | IP | 42.1 | 0.001 |
| | 1.5 mg/ml | 8 | IP | 33.3 | 0.001 |

FIG. 18 illustrates the distribution of scores over time in the experiment. From these data it appears that the effect of 10150 occurs in the initiation of mucositis, reducing the incidence of ulcers at peak time, approximately day 14. FIG. 19 displays the effect on 10150 on the percent of days with scores ≥3 (i.e. severe mucositis).

These findings indicated that 10150 markedly reduces the severity of mucositis associated with radiation therapy as is used in cancer therapy. This effect was most evident in groups treated with IP administration. However, as can be seen from FIG. 19, while not statistically significant, the high dose topical treatment tended to reduce mucositis severity as well, suggesting that higher concentrations used topically, with correspondingly higher tissue concentrations, could result in effects similar to that seen with IP administration.

All documents cited above are hereby incorporated in their entirety by reference.

One skilled in the art will appreciate from a reading of this disclosure that various changes in form and detail can be made without departing from the true scope of the invention.

What is claimed is:

1. A method of treating lung cancer in a mammal, the method comprising:

administering to a mammal in need thereof a radiation therapy and a compound having the formula:

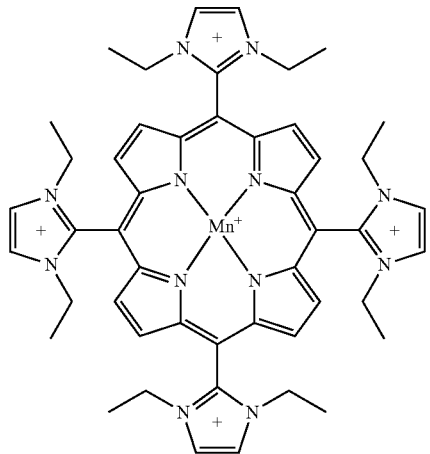

or a pharmaceutically acceptable salt thereof.

2. The method according to claim 1, wherein the mammal is a human.

3. A method of treating radiation-induced lung injury in a mammal in need thereof comprising administering to said mammal a compound having the formula:

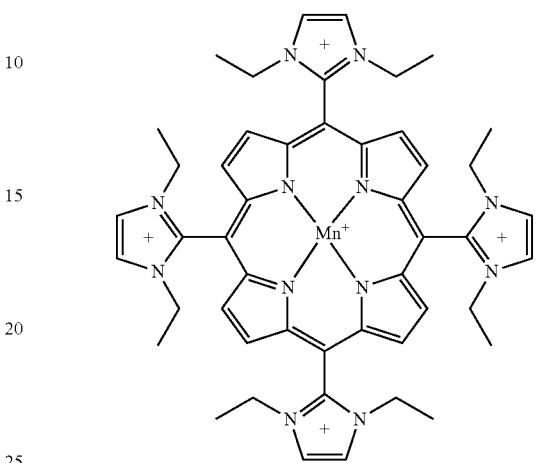

or a pharmaceutically acceptable salt thereof.

4. The method according to claim 3, wherein the mammal is a human.

* * * * *